(12) United States Patent
Georg et al.

(10) Patent No.: US 6,603,015 B2
(45) Date of Patent: Aug. 5, 2003

(54) SYNTHESIS OF EPOTHILONES

(75) Inventors: Gunda I. Georg, Lawrence, KS (US); Sajiv K. Nair, Lawrence, KS (US); Emily Reiff, Lawrence, KS (US); Ashok Rao Tunoori, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 36 days.

(21) Appl. No.: 10/014,754

(22) Filed: Dec. 11, 2001

(65) Prior Publication Data

US 2002/0156289 A1 Oct. 24, 2002

Related U.S. Application Data

(63) Continuation-in-part of application No. 09/798,196, filed on Mar. 2, 2001, now Pat. No. 6,457,303, which is a continuation of application No. 09/280,207, filed on Mar. 29, 1999, now Pat. No. 6,211,412.

(51) Int. Cl.[7] .................. C07D 277/22; C07D 263/30; C07C 49/213; C07C 49/04; C07C 31/18
(52) U.S. Cl. .................. 548/203; 548/235; 568/308; 568/309; 568/382; 568/662; 568/672; 568/814; 568/852; 435/451
(58) Field of Search ................ 568/308, 309, 568/382, 662, 672, 814, 852; 548/203, 235; 435/451

(56) References Cited

U.S. PATENT DOCUMENTS 5,580,898 A    12/1996  Trojanowski et al.
6,156,905 A  * 12/2000  Schinzer et al.
6,211,412 B1 *  4/2001  Georg et al.
6,457,303 B1 * 10/2002  Georg et al.

OTHER PUBLICATIONS

Liming et al; Tetrahedron, vol. 49 (No. 10), pp. 1997–2010, published 1993.
Williams et al; Tetrahedron Letters, vol. 36 (No. 31), pp 5461–5464, published 1995.
Carey et al; Advanced Organic Chemistry, third edition, p. 677, published 1990.
Michaelis et al.; Journal of Neurochemistry; pp 1623–1627, published 1998.
Chauhan et al; Tetrahedron Letters, vol. 35 (No. 12); pp 1825–1828; published 1994.
Kerdesky et al; Organic Chemistry; vol. 58; pp 3516–3520; published 1993.
Huet et al; Tetrahedron; vol. 29; pp 479–485; published 1973.

* cited by examiner

Primary Examiner—Johann Richter
Assistant Examiner—Sikarl A. Witherspoon
(74) Attorney, Agent, or Firm—Hovey Williams LLP

(57) ABSTRACT

Commercially feasible methods for synthesizing various epothilones precursors needed for the preparation of final epothilones are provided, including techniques for the synthesis of epothilone segment A and C precursors. Segment C precursors are prepared using starting nitriles, which can alternately be oxidized to ketones and converted, or reacted to form the diol with subsequent conversion to the segment. Segment A precursors are prepared by reacting a starting enone with a chiral catalyst to give an intermediate alcohol in high enantiomeric excess, followed by conversion of the alcohol to the desired Segment A precursor.

23 Claims, No Drawings

SYNTHESIS OF EPOTHILONES

RELATED APPLICATION

This is a continuation-in-part of application Ser. No. 09/798,196, filed Mar. 2, 2001, now U.S. Pat. No. 6,457,303, which is a continuation of application Ser. No. 09/280,207, filed Mar. 29, 1999, now U.S. Pat. No. 6,211,412, issued Apr. 3, 2001.

BACKGROUND OF THE INVENTION

1. Field of the Invention

The present invention is broadly concerned with methods for synthesizing various epothilone segments or precursors (either naturally occurring or analogs thereof) which can be used for the efficient synthesis of complete epothilones.

2. Description of the Prior Art

The epothilones (16-membered macrolides which were initially isolated from the myxobacterium *Sorangium cellulosum*) represent a class of promising anti-tumor agents, and have been found to be potent against various cancer lines, including breast cancer cell lines. These agents have the same biological mechanism of action as Taxol, an anti-cancer drug currently used as a primary therapy for the treatment of breast cancer. Other potential applications of the epothilones could be in the treatment of Alzheimer's disease, malaria and diseases caused by gram-negative organisms. Other cancers such as ovarian, stomach, colon, head and neck and leukemia could also potentially be treated. The epothilones also may have application in the treatment of arthritis.

In comparison to Taxol®, the epothilones have the advantage of being active against drug-resistant cell lines. Drug resistance is a major problem in chemotherapy and agents such as the epothilones have overcome this problem and hold great promise as effective agents in the fight against cancer.

In addition, the poor water solubility of Taxol® has led to the formulation of this drug as a 1:1 ethanol-Cremophor concentrate. It has been determined that the various hypersensitive reactions in patients such as difficulty in breathing, itchiness of the skin and low blood-pressure are caused by the oil Cremophor used in the formulation. The epothilones are more water soluble than Taxol® which has positive implications in its formulation. Further advantages of the epothilones include easy access to multi-gram quantities through fermentation procedures. Also the epothilones are synthetically less complex, thus structural modifications for structure activity relationship studies are easily accessible.

The epothilones exhibit their activity by disrupting uncontrolled cell division (mitosis), a characteristic of cancer, by binding to organelles called microtubules that are essential for this process. Microtubules play an important role in cell replication and disturbing the dynamics of this component in the cell stops cell reproduction and the growth of the tumor. Antitumor agents that act on the microtubule cytoskeleton fall into two general groups: (1) a group that inhibits microtubule formation and depolymerizes microtubules and, (2) a group that promotes microtubule formation and stabilizes microtubules against depolymerization. The epothilones belong to the second group and have displayed cytotoxicity and antimitotic activity against various tumor cell lines.

It has been demonstrated on the basis of in vitro studies that the epothilones, especially epothilone B, are much more effective than Taxol® against the multi-drug resistant cell line KBV-1. Preliminary in vivo comparisons with Taxol® in CB-17 SCID mice bearing drug-resistant human CCRF-CEM/VBL xenografts have shown that the reduction in tumor size was substantially greater with epothilone B in comparison to Taxol®.

In light of the great potential of the epothilones as chemotherapeutic agents, there is a need for techniques allowing the practical, large scale, economical synthesis thereof. Furthermore, there is a need for synthetic methods which facilitate the preparation of various homologs and analogs of the known epothilones, and those having affinity labels allowing study of the binding interactions of these molecules.

SUMMARY OF THE INVENTION

The present invention overcomes the problems outlined above, and provides various practical, commercially feasible synthetic routes for the production of important epothilone precursors or segments in high yield. The invention is particularly concerned with the synthesis of the precursors or segments C, D (which is a combination of segments B and C) and vinyl halide epothilone precursors.

In a first aspect of the invention, a C1–C6 segment C epothilone precursor of the formula

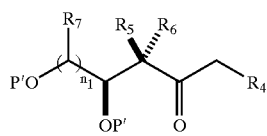

I is synthesized using a Noyori reduction reaction. In the foregoing formula, $n_1$ is an integer from 0–4, $R_4$ is selected from the group consisting of H, C1–C10 straight and branched chain alkyl groups, substituted and unsubstituted benzyl groups, and C1–C10 alkoxy groups, $R_5$ and $R_6$ are each individually and respectively selected from the group consisting of H, substituted and unsubstituted aryl and heterocyclic groups, C1–C10 straight and branched chain alkyl groups, and substituted and unsubstituted benzyl groups, $R_7$ is H or straight or branched chain C1–C10 alkyl groups, and P' is a protective group (as used herein, P' is any suitable protective group, and where more than one P' is in a single formula, the protective group may be the same or different).

The method comprises the steps of first providing a β-keto ester of the formula

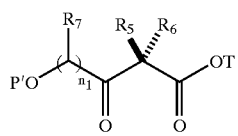

II where $n_1$, $R_5$, $R_6$, $R_7$ and P' are as defined above, and T is an alkyl group. This β-keto ester is then preferentially hydrogenated at the C3 keto group to form the corresponding hydroxyester. This is accomplished by reacting the β-keto ester with a hydrogenating agent in the presence of an asymmetric organometallic molecular catalyst comprising a metal atom or ion having one or more chiral ligands coupled thereto. The synthesis is completed by then converting the hydroxyester to the epothilone precursor.

More preferably, $n_1$ is an integer from 0–4, $R_5$, $R_6$ and $R_7$ are each individually and respectively selected from the group consisting of H and the straight and branched chain C1–C4 lower alkyls, and the protective group is benzyl. In terms of preferred process parameters, the hydrogenating agent is preferably $H_2$ and the hydrogenating step is carried out at a pressure of from about 30–100 psi, more preferably 50–75 psi, and at a temperature of from about 40–100° C., more preferably from about 50–75° C. The reaction is normally allowed to proceed for a period of from about 12 hours to 5 days, and more usually for about 2–5 days. Typically, the reaction mixture is agitated during the hydrogenating step.

The catalyst used in the hydrogenation reaction is preferably one of the well-known Noyori catalysts such as $RuBr_2(S)$-binap. However, a variety of other catalysts of this type can also be employed. The catalyst is generally used at a level of from about 1–25 mol % in the reaction mixture.

In order to complete the reaction sequence, the hydroxyester resulting from the Noyori reduction is converted to the epothilone precursor segment C. A number of routes can be used to effect this conversion. Preferably, however, the conversion involves: (1) removing the P' protecting group from the hydroxyester to form a diol; (2) protecting the oxygen atoms of the diol, forming a protected diol; (3) reducing the ester function of the protected diol to a primary alcohol; (4) oxidizing the primary alcohol to the corresponding aldehyde; (5) reacting the aldehyde with a Grignard reagent having the $R_4$ group coupled thereto to form a secondary alcohol; and (6) oxidizing the secondary alcohol to form the final epothilone precursor.

Preferably, the P' removal step involves reacting the hydroxyester with hydrogen in the presence of a catalyst (e.g., $Pd(OH)_2$ or Pd/C) at a pressure of from about 40–100 psi. The oxygen atom protecting step comprises reacting the diol with TBS chloride in a compatible solvent (i.e., one that will not interfere with the desired reaction) at a temperature of from about 40–100° C. for a period of from about 30–60 hours. The ester function reduction step is preferably carried out by reacting the protected diol with the reducing agent DIBAL-H at a temperature of from about −20 to −85° C. The oxidation of the primary alcohol is carried out most conveniently using 4-methylmorpholine N-oxide and a catalytic amount of tetrapropylammonium perruthenate. The Grignard reaction serving to attach the $R_4$ group is entirely conventional and well within the skill of the art; likewise, the final oxidation of the secondary alcohol is trivial using the aforementioned oxidation procedure, i.e., NMO and TPAP.

The C1–C6 Formula I segment C can also be produced by a synthesis wherein a nitrile compound of the formula

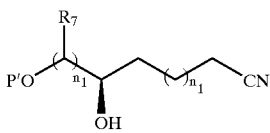

III where P', $R_7$ and $n_1$, are as defined above and the value of each $n_1$ may be the same or different, is alkylated to yield a dialkylated nitrile compound of the formula

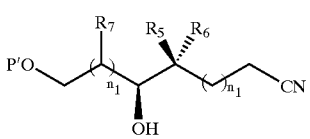

IV where P', $R_5$, $R_6$, $R_7$, and $n_1$ are as defined above and the value of $n_1$ may be the same or different; and the dialkylated compound is then converted to the desired C1–C6 segment C epothilone precursor.

The converting step preferably involves oxidizing the dialkylated compound III to yield a ketone of the formula

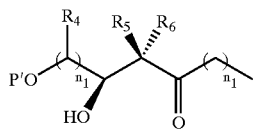

V where P', $R_4$, $R_5$, $R_6$, and $n_1$ are as defined above and the value of each $n_1$ may be the same or different, and converting the ketone to the C1–C6 epothilone precursor.

Alternately, the dialkylated nitrile compound defined above may be treated by deprotecting the nitrile to yield a diol compound having the formula

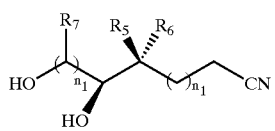

VI where $R_5$, $R_6$, $R_7$ and $n_1$ are as defined above and the value of each $n_1$ may be the same or different, and thereafter converting the diol compound to the C1–C6 epothilone precursor.

A still further synthesis of the Formula I C1–C6 segment C precursor comprises providing an ester compound of the formula

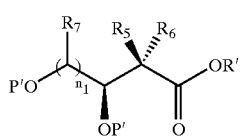

VII where $R_5$, $R_6$, $R_7$, P' and $n_1$, and R' is a C1–C10 straight or branched chain alkyl group reacting the ester compound VIII with a sulfone to acylate the ester, and thereafter desulfonating the acylated ester to obtain the desired segment C epothilone precursor. The sulfone is preferably of the formula

$X_1$—$SO_2$—$R_4$ VIII where $R_4$ is defined above and $X_1$ is selected from the group consisting of unsubstituted aryl and heterocyclic groups. The most preferred sulfone is ethyl phenyl sulfone.

In another aspect of the invention, a method is provided for the production of D precursors, which are a combination of segments B and C. The segment C precursors are of course produced as outlined above. Segment B precursors are of the formula

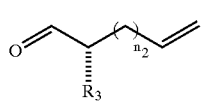

IX where $n_2$ is an integer from 1–4, and $R_3$ is selected from the group consisting of H, C1–C10 straight and branched chain alkyl groups, substituted and unsubstituted benzyl groups, and C1–C10 alkoxy groups. This segment can be efficiently produced using known techniques.

The segments B and C are connected by first reacting the segment C precursor with a base to form an enolate, followed by reacting the enolate with the segment B. These reactions are generally carried out by initially cooling the base to a temperature of about −75° C., adding the segment C precursor and elevating the temperature of the mixture to about −40° C., then recooling the mixture to at least about −75° C. and adding the precursor segment B thereto.

The invention also is concerned with a method of synthesizing vinyl halide epothilone precursors having the general formula

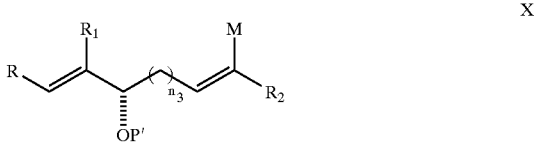

X where $n_3$ is an integer from 1–4, R is selected from the group consisting of C4–C8 cycloalkyl, and substituted and unsubstituted aromatic and heteroaromatic groups, $R_1$ and $R_2$ are each individually and respectively selected from the group consisting of H, C1–C10 straight and branched chain alkyl groups, substituted and unsubstituted benzyl groups, and C1–C10 alkoxy groups, P' is a protecting group, and M is either bromine or iodine. This reaction involves first providing an alkynyl ketone of the formula

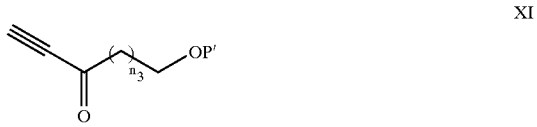

XI wherein $n_3$ and P' are as previously defined. Thereafter, the alkynyl ketone is asymmetrically reduced to create the alcohol form of the alkynyl ketone. This alcohol form is then reacted with a reagent system selected from the group consisting of $(R_1)_3Al$ and zirconocene dichloride or stannyl cupration reagent and $R_1$-halide to form a vinyl metal species. The vinyl metal species is then reacted with an aryl or vinyl halide to form an allyl alcohol. This allyl alcohol is then converted to the vinyl halide epothilone precursor.

Normally, the asymmetric reduction step involves creating the reduced form of the alkynyl ketone and the resulting alcohol is protected using TBS as a protecting agent. The $R_1$-halide is selected from the group consisting of $R_1Br$ and $R_1I$. The conversion step preferably includes the step of initially converting the allyl alcohol to an alkynyl stannane, reducing the stannane with chlorohydridozirconocene to form a 1,1-dimetallo Zr—Sn species. The dimetallo species is then hydrated to form a vinyl stannane, which is then quenched with either iodine or bromine. Alternately, the conversion step may be accomplished by transmetallating the dimetallo species with an organocuprate, quenching with an alkyl-$R_2$-OTf, and final quenching with either iodine or bromine incorporating the $R_2$ group.

Preferred vinyl halide C12–C20 epothilone precursors of the formula

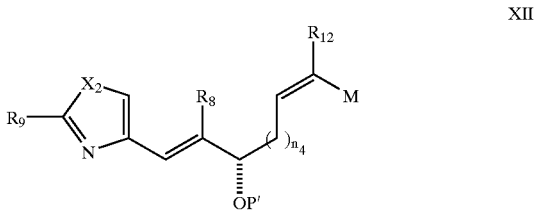

XII where $R_8$ is selected from the group consisting of H, C1–C4 straight or branched chain alkyl, alkenyl or alkynyl groups, $R_9$ is selected from the group consisting of H, C1–C10 straight and branched chain alkyl, alkenyl, alkynyl, hydroxyalkyl, hydroxyalkenyl or hydroxyalkynyl groups, substituted and unsubstituted cyclic, heteroxylic and aryl groups, $R_{12}$ is selected from the group consisting of H, C1–C10 straight and branched chain alkyl groups, substituted and unsubstituted benzyl groups, and C1–C10 alkoxy groups, $X_2$ is O or S, $n_4$ is an integer which ranges from 1 to 4, P' is a protective group and M is either iodine or bromine, may be produced as follows.

First, an alcohol of the formula

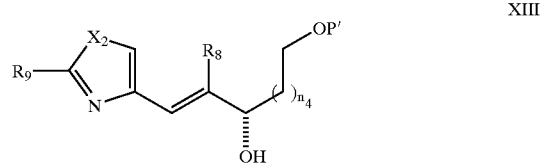

XIII where $R_8$, $R_9$, $X_2$, $n_4$ and P' are as defined above, is converted to the C12–C20 epothilone segment A. This method preferably comprises the steps of:

providing an enone compound of the formula

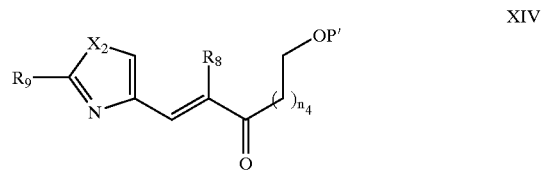

XIV where $R_8$, $R_9$, $X_2$, P' and $n_4$ are as defined above, and asymmetrically reducing the enone compound XIV in the presence of a chiral catalyst to obtain the alcohol, compound XIII. The alcohol compound XIII is then protected at the C15 alcohol position, followed by known conversion steps to precursor Formula XII.

The enone compound XIV is preferably obtained by reacting in a basic reactive medium starting aldehyde compound of the formula

XV where $R_9$ and $X_2$ are as defined above, with a phosphonate compound of the formula

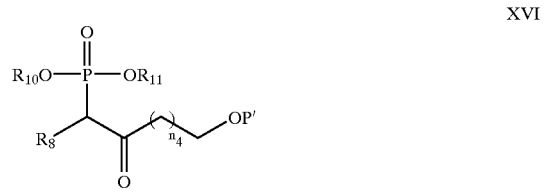

XVI where $R_8$, P' and $n_4$ are as defined above, and $R_{10}$ and $R_{11}$ are individually selected from the group consisting of C1–C4 straight or branched chain alkyl groups. In particularly preferred forms, $R_8$ and $R_9$ are each H, X is S, $n_4$ is 1, and P' is TBS. The chiral catalyst is preferably (R)-B-Me-CBS-oxazaborolidine.

A still further method of synthesizing the preferred C12–C20 epothilone precursors of Formula XII described immediately above involves conducting an aldol condensation reaction using an aldehyde with an enolate anion to give a β-keto alcohol; this alcohol is then oxidized to the ester form followed by an asymmetric reduction to yield a chiral alcohol. Preferably, the method comprises providing an aldehyde of the formula

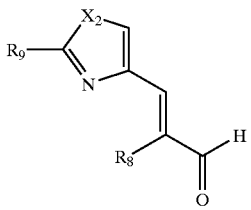

XVII where $R_8$, $R_9$ and $X_2$ are as defined above, reacting this aldehyde with an acetate of the formula

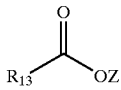

XVIII where $R_{13}$ is a methyl group, Z is a C1–C4 straight or branched chain alkyl group or a substituted or unsubstituted benzyl group in a basic reaction mixture to yield a β-hydroxyester of the formula

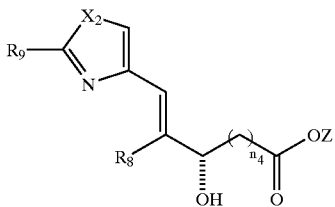

XIX where $R_8$, $R_9$, $X_2$, and Z are as defined above.

The β-hydroxyester is then oxidized to the corresponding β-ketoester of the formula

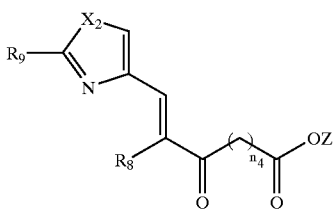

XX where $R_8$, $R_9$, $X_2$, and Z are as defined above. Next, β-ketoester is hydrogenated to form a chiral alcohol of the formula

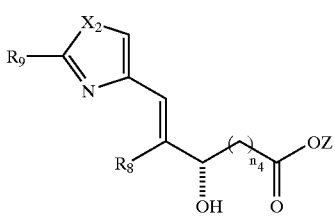

XXI where $R_8$, $R_9$, $X_2$, and Z are as defined above, by reacting the β-ketoester with a hydrogenating agent in the presence of asymmetric organometallic molecular catalyst comprising a metal atom or ion having one or more chiral ligands coupled thereto. Finally, the chiral alcohol is converted to the C12–C20 epothilone of Formula XII.

In preferred forms, the acetate is ethyl acetate, and the aldehyde and acetate are reacted in the presence of an alkali metal diisopropyl amide in a solvent selected from the group consisting of THF, a mixture of t-butanol and t-butoxide, sodium ethoxide, and ethanol. The reaction temperature is preferably from about −50 to −125° C. The β-ketohydroxyester is preferably oxidized using an alkali metal or alkaline earth metal oxide or hydroxide. The hydrogenating step preferably uses hydrogen and is carried out at a pressure of from about 30–100 psi, and a temperature from about 40–100° C.

DETAILED DESCRIPTION OF THE PREFERRED EMBODIMENT

The molecular architecture of the representative epothilones (Formulae A-B) reveals three essential domains. These include the two chiral domains, namely the C1–C8 polypropionate region and the C12–C15 region, and the achiral spacer C9–C11 which unites the chiral domains. Additional structural features include a thiazole moiety, the C16 double bond, a methyl group at C4 and a cis-epoxide moiety (C12–C13) in the epothilones of Formula A. In the following formulae A and B, $n_1$ is an integer from 0–4, $n_2$ and $n_3$ are each respectively integers from 1–4, R is selected from the group consisting of C4–C8 cycloalkyl, and substituted and unsubstituted aromatic and heteroaromatic groups, $R_1$, $R_2$, $R_3$ and $R_4$ are each individually and respectively selected from the group consisting of H, C1–C10 straight and branched chain alkyl groups, substituted and unsubstituted benzyl groups, and C1–C10 alkoxy groups, $R_5$ and $R_6$ are each individually and respectively selected from the group consisting of H, substituted and unsubstituted aryl and heterocyclic groups, C1–C10 straight and branched chain alkyl groups, and substituted and unsubstituted benzyl groups, $R_7$ is H, or straight or branched chain C1–C10 alkyl groups, X is either oxygen or NH, and Y is either oxygen or $H_2$.

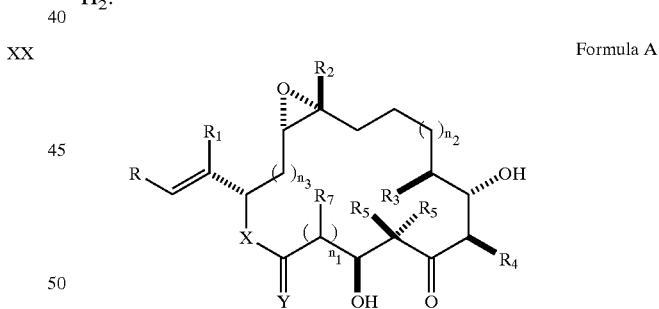

Formula A

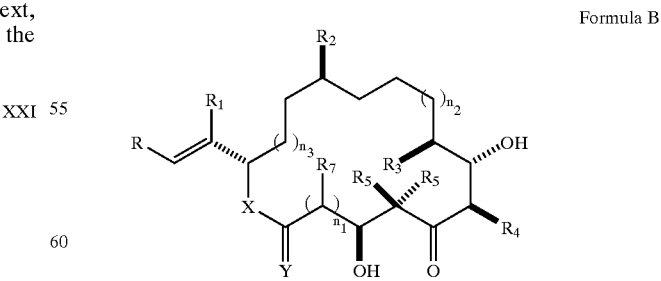

Formula B

Scheme 1 below outlines a retrosynthetic analysis respecting the total synthesis of the epothilones of Formula A in accordance with the invention, where each $n_1$ and $n_2$ equal 1, R is 2-methyl-thiazol-4-yl, $R_1$, is methyl, $R_2$ is H or methyl, $R_3$, $R_4$, $R_5$ and $R_6$ are methyl, $R_7$ is H, and X and Y are oxygen. Standard epoxidation and macrolactonization strategies are used for the formation of the C12–C13 epoxide moiety and the 16-membered macrolide. The analysis for other analog epothilones of Formula A is identical, and also for the epothilones of Formula B and its analogs, with the epoxidation step being omitted.

A novel route to a Formula I C1–C6 segment (labeled C in Scheme 1) utilizes a stereoselective hydrogenation reaction, i.e., a Noyori reduction.

Scheme 1

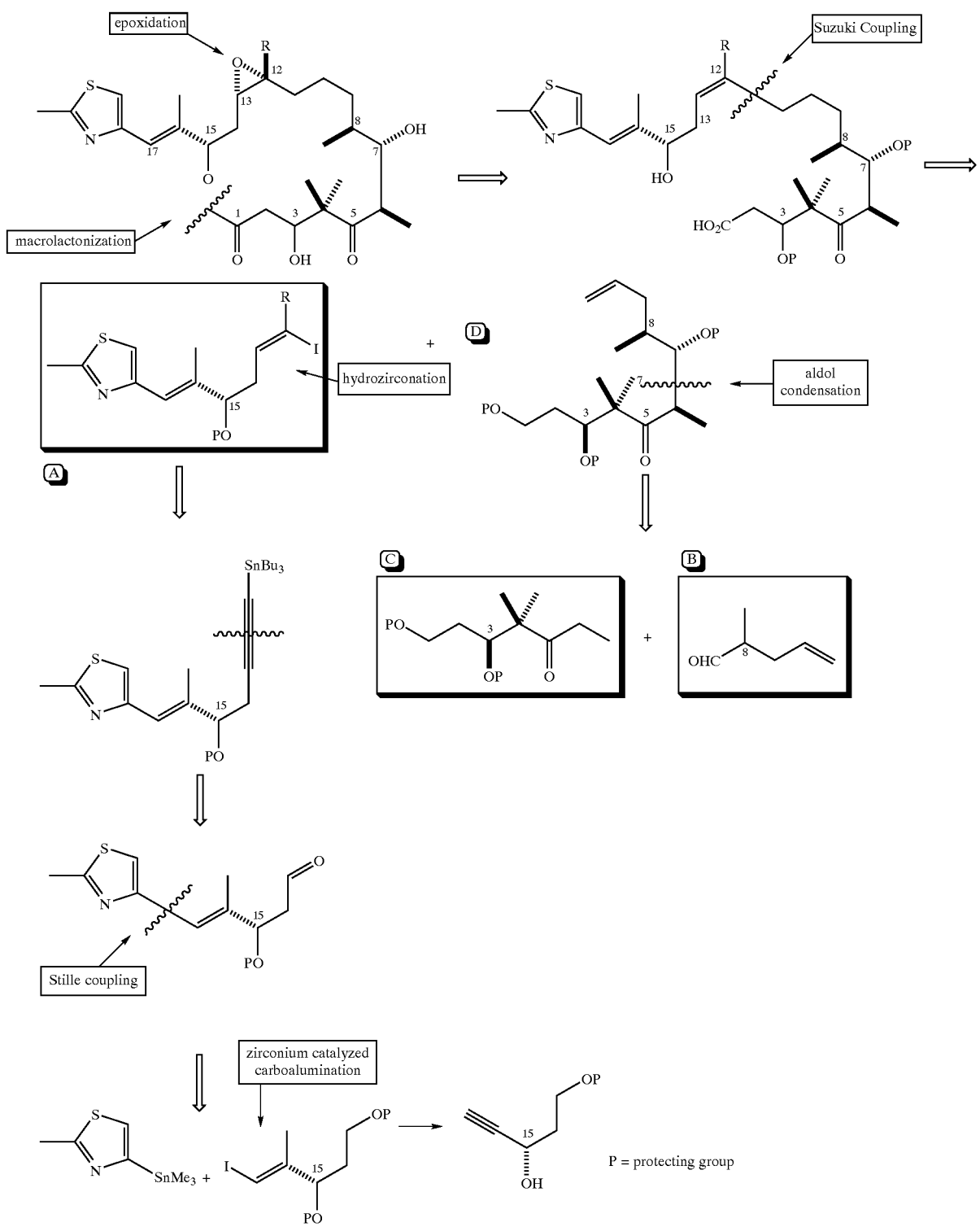

Synthesis of Segment C (C1–C6 of Formula A)

The invention makes it possible to synthesize several analogs of segment C as set forth in Formula I with various chain elongations and/or substitutions at C2 and substitutions at the α-carbon relative to the keto group. It also allows for, as mentioned before, modifications at the carbon atom between the keto and the protected secondary hydroxy group with other groups. These chain extensions and substitutions are illustrated by a general Formula I, previously identified. The synthesis of these modified derivatives can be achieved utilizing chemistry exemplified in the synthesis of segment C in the Schemes described below. These modified segments can then be utilized in the total synthesis of various analogs of epothilones.

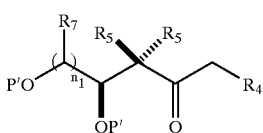

I

The synthesis of the Forumula I segment has been accomplished via unique and complementary routes, detailed in Schemes 2 and 3 below, which illustrates the synthesis of the naturally occurring segment C. A novel step in the synthesis of the C1–C6 segment utilizes the Noyori hydrogenation of β-keto ester 4 to generate the requisite stereochemistry at C3. This Noyori hydrogenation (Noyori, R. et al., *Asymmetric Hydrogenation of, β-Keto Carboxylic Esters. A Practical, Purely Chemical Access to β-Hydroxy Esters in High Enantiomeric Excess*, J. Am. Chem. Soc. 109:5856–5858 (1987)) provides the required enantiomer with high selectivities (92–95% enantiomeric excess). The use of a Noyori hydrogenation reaction permits large, commercial scale production of various segment C precursors.

The required β-keto ester 4 is obtained in two steps from the readily available starting material 3-benzyloxypropionic acid (2). Asymmetric hydrogenation of 4 in methanol using RuBr$_2$(S)-binap as catalyst at 60 psi gives the β-hydroxyester 5 in 71–92% yield (92–95% ee). Deprotection of the benzyl ether and bis-silylation of the resultant diol 6 provides ester 7. The ester is reduced to the known primary alcohol 8 using DIBAL-H. The alcohol is then oxidized to the known aldehyde 9 using a previously unreported oxidation procedure. The aldehyde is then reacted with EtMgBr using a reported procedure (Claus, et al., *Synthesis of the C1–C9 Segment of Epothilons*, Tetrahedron Lett., 38:1359–1362 (1997)) to give the known secondary alcohol 10 in 65% yield. This alcohol is then oxidized to the C1–C6 segment C using TPAP and NMO.

In summary, although segment C is a key synthon in previously reported total syntheses (Nicolaou, et al., *Total Syntheses of Epothilones A and B via a Macrolactonization-Based Strategy*, J. Am. Chem. Soc., 119:7974–7991 (1997)) of the epothilones, the synthetic route utilizing the asymmetric Noyori hydrogenation is unique.

The alternate route toward segment C precursors allows for the introduction of affinity labels and modifications at the C4 position as shown in Scheme 3. Applying the Noyori reduction to the known unsubstituted β-keto ester 11 provides a building block that can be used for the modifications at C4 of the epothilones. This Scheme accordingly allows for modification of the epothilones and gives a more general route to introduce a variety of substituents at this position.

Thus, the Noyori hydrogenation of β-keto ester 11 yields the known β-hydroxy ester 12 (Ali, et al., *Formal Syntheses of Cryptophycin 1 and Arenastatin A*, Tetrahedron Lett., 38:1703–1706 (1997)) in 97% yield (in 97% enantiomeric excess). The Frater alkylation of β-hydroxy ester 12 yields the previously reported α-methyl analogue 13 (Ali, et al., *Formal Syntheses of Cryptophycin 1 and Arenastatin A*, Tetrahedron Lett., 38:1703–1706 (1997)) in 71% yield (98% diastereomeric excess). A second Frater alkylation of hydroxyester 13 gave bis-dimethyl derivative 5 in 59% yield which was then converted to epothilone segment C by the chemistry shown in Scheme 2. At this stage, other substituents such as benzyl, allyl and other C1–C6 alkyl groups can be introduced by using other electrophiles in the second Frater alkylation in place of iodomethane. The novel aspect about this alternate route to segment C is the ability to alter the substituents at the C4 position of the epothilones using the aforementioned Frater alkylation strategy.

Scheme 2,3

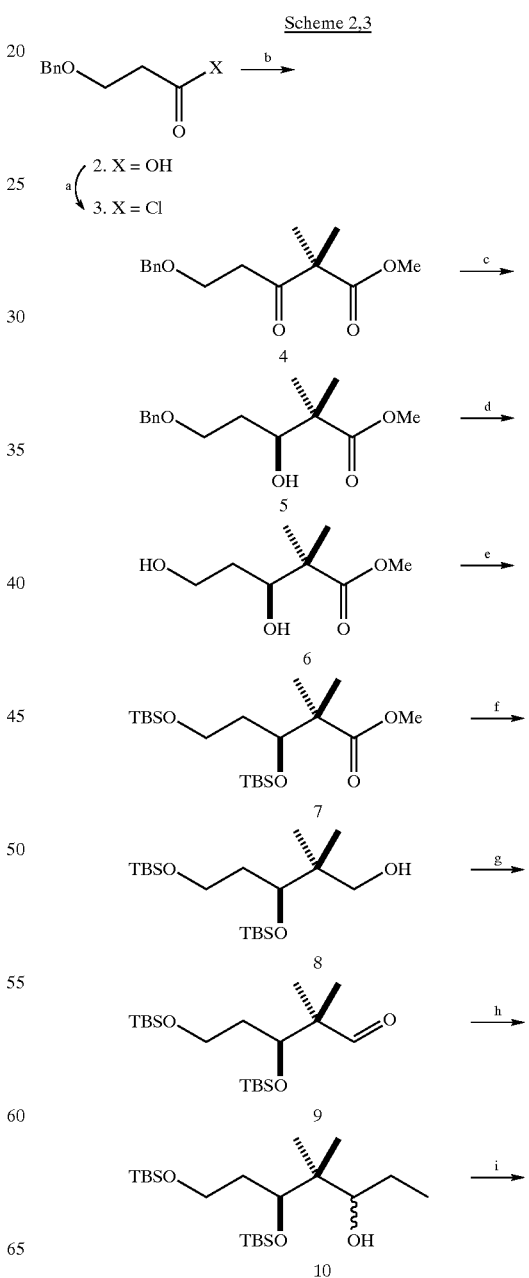

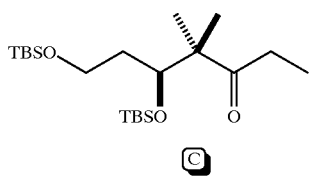

a) (COCl)₂, CH₂Cl₂, 99%;
b) methyl isobutyrate, LICA, THF, -78° C., 65%;
c) RuBr₂, (S)-binap, H₂, MeOH, 65 psi, 70° C., 71%, (92% ee);
d) H₂, Pd(OH)₂, THF, 90%;
e) TBSCl, imidazole, DMF, 60° C., 78%;
f) DIBAL-H, CH₂Cl₂, -78° C., 95%;
g) TPAP, NMO, 4 AMS, CH₂Cl₂, 85%;
h) EtMgBr, Et₂O, -78° C., 65%;
i) same as g, 92%.

Scheme 3

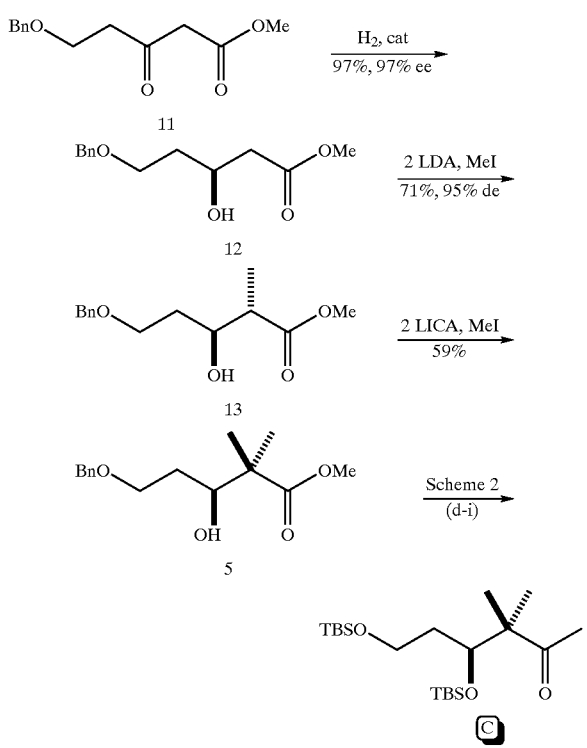

In another aspect of the invention, the synthesis of exemplary segment C (and of course all of the other segment C analog precursors of Formula I) utilizes a starting material which can be obtained from lactose or malic acid and circumvents the need to construct the C3 stereochemistry using an asymmetric synthesis. This technique gives access to the C1–C6 segment of the epothilones by a concise route set forth in Scheme 3A.

Scheme 3A

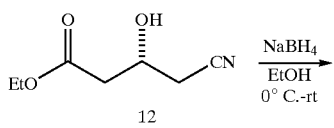

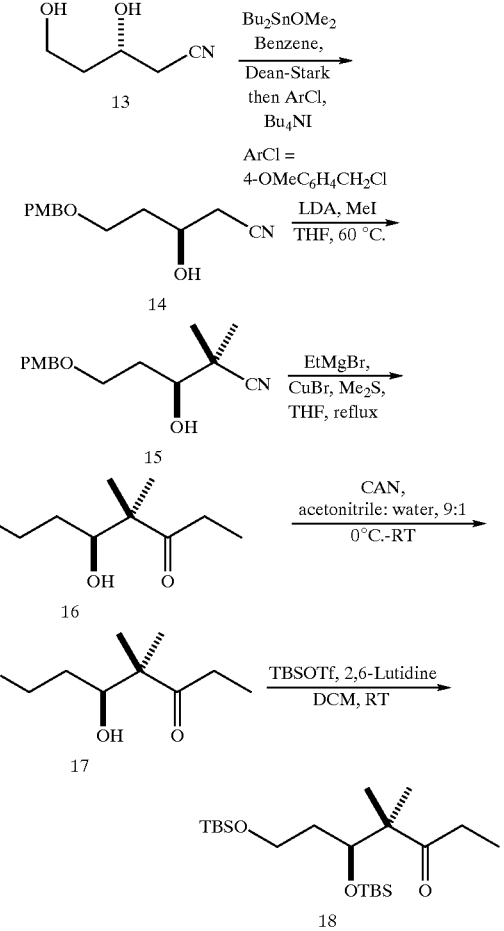

The Scheme 3A synthesis employs ethyl-(R)-4-cyano-3-hydroxybutanoate 12 as starting material. Selective reduction of the ester functionality using sodium borohydride in ethanol from 0° C. to room temperature overnight gave (S)-3,5-dihydroxyvaleronitrile 13.

The product 13 was then protected at its free 4-hydroxyl group as a p-methoxybenzyl ether by forming a dibutyl tin acetal with dibutyltin dimethoxide in refluxing benzene, followed by treatment with p-methoxybenzyl chloride and tetrabutylammonium iodide at 60° C. to give the primary ether derivative 14 in 61% yield.

The nitrile 14 is then alkylated using LDA and methyl iodide. The enolate of the nitrile generated using LDA is warmed to 60° C. before the addition of methyl iodide to ensure dialkylation to give (S)-2,2-dimethyl-3-hydroxy-5-p-methoxybenzyloxy-valeronitrile 15 in 76% yield.

The dialkylated product 15 thus obtained is then refluxed with ethyl magnesium bromide in a THF solution with a catalytic quantity of copper bromide-dimethylsulfide complex and the resulting imine hydrolyzed in situ with 0.5 N aqueous citric acid solution for 5 hrs to give ketone 16. Deprotection of the PMB group on the ketone 16 with ceric ammonium nitrate with a 1:9 water:acetonitrile solvent mixture followed by protection of the diol with TBSOTf and 2,6-lutidine gave the ketone 18 which constitutes segment C, the C1–C6 carbon skeleton of the epothilones.

An even more preferred synthesis of the C1–C6 segment C precursors is a two-step, one-pot conversion of an intermediate methylester to the ethyl ketone using a sulfone anion to acylate the ester, followed by desulfonylation to provide segment C using sodium amalgam. This one-pot conversion achieves 90% yield and shortens the synthesis significantly. This preferred synthesis is set forth in the following Scheme 3B; again this scheme may be readily modified to obtain desired analogs defined by Formula I.

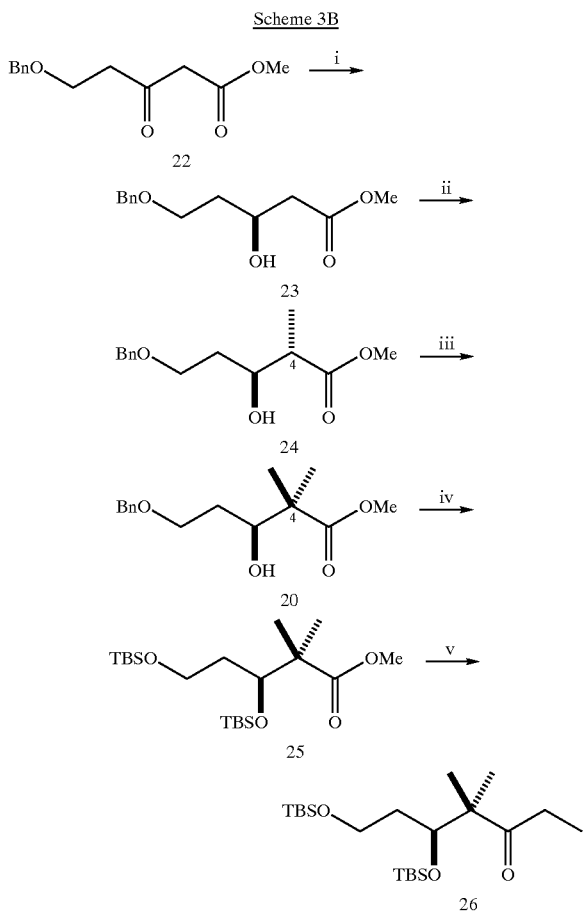

i) RuBr$_2$(S)binap, H$_2$, MeOH, 50 psi, 50° C., 16 h, 97%, 97% ee;
ii) LDA (2 eq), MeI, HMPA, THF, -78° C.->-20° C., 16 h, 75%, 95 % de;
iii) LICA (2 eq), MeI, HMPA, THF, -78° C.->rt, 16 h, 59%;
iv) a) H$_2$, Pd(OH)$_2$, THF, 50 psi, rt, 16 h, 98%;
   b) TBSOTf, 2,6-lutidine, CH$_2$Cl$_2$, 0° C.->rt, 16 h, 90%;
v) a) PhSO$_2$Et(5.5 eq), n-BuLi (5 eq), THF, -78° C.->rt, 18 h;
   b) Na(Hg), Na$_2$HPO$_4$, MeOH, 0° C., 1h, 90% (2 steps).

Synthesis of Segment B (C7–C11 of Formula A)

The synthesis of the C7–C11 segment B is preferably achieved using previously reported chemistry (Lin, *Efficient Total Syntheses of Pumiliotoxins A and B, Applications of Iodide-Promoted Iminium Ion-Alkyne Cyclization in Alkaloid Construction*, J. Am. Chem. Soc., 118:9062–9072 (1996)) and is outlined in exemplary Scheme 4, which is precursor of a naturally occurring epothilone.

Scheme 4

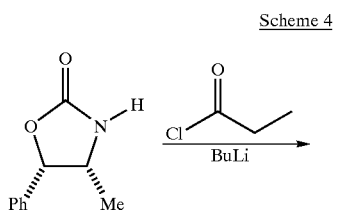

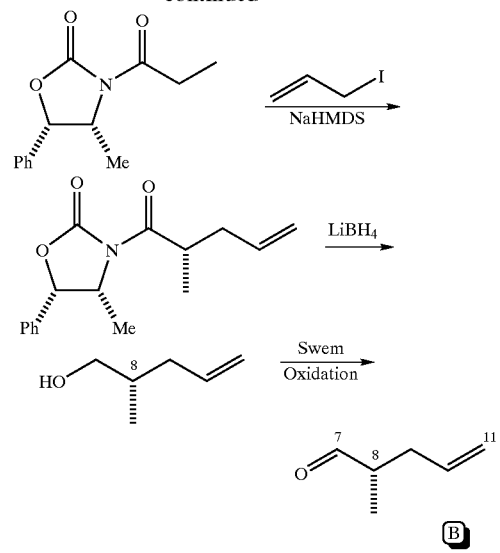

This synthesis can also be used to introduce various chain-elongations on this segment and to introduce various other substituents at C-8. These modifications can be illustrated by Formula IX (Segment D), wherein $n_2$ and $R_3$ are as defined previously. Their synthesis can be achieved using chemistry exemplified in the synthesis of segment B in Scheme 4. Again, these modified segments can then be utilized in the total synthesis of various analogs of epothilones.

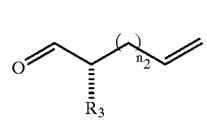

IX

Synthesis of Segment D (C1–C11 of Formula A) via Aldol Reaction

The connection of the two segments C and B utilizes a highly diastereoselective aldol reaction, exemplified in Scheme 5 showing the connection of the two precursors B and C of a naturally occurring epothilone. When the C1–C6 ketone segment C is treated with abase, for example lithium diisopropylamide and the resultant enolate reacted with C7–C11 aldehyde segment B, a single desired diastereomer 14 was observed in 65% yield. This diastereoselectivity is believed to arise from a favorable nonbonding interaction between the C10–C11 double bond and the carbonyl group of the aldehyde that gives rise to the desired diastereomer. After the connection is made, the resultant secondary alcohol is protected as the corresponding tert-butyldimethylsilyl ether.

Similar chemistries would apply for the connection of modified segments C and B of the type discussed previously and emplified by Formulae C and D.

Scheme 5

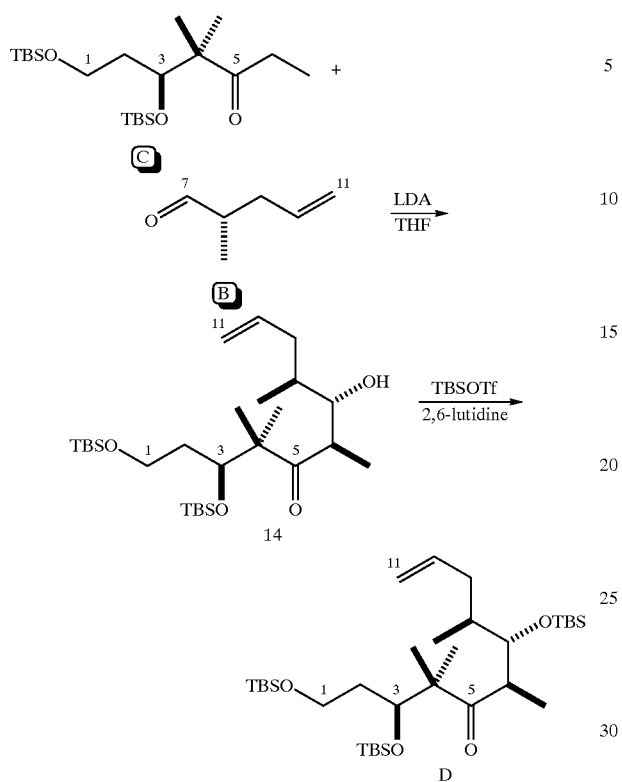

Proposed Synthesis of Segment A (C12–C20 of Formula A)

The invention also provides a new route to the C12–C20 segment (segment A of the naturally occurring epothilone), and corresponding analogs thereof. This involves new ways to set the C16–C17 trisubstituted double bond and the C12–C13 cis-double bond, which serves as precursor to the cis-epoxide at C12–C13 in the epothilones.

Stereoselective Construction of C16–C17 of Trisubstituted Olefin and Introduction of Thiazole in Formula A The introduction of the thiazole moiety draws upon zirconium-catalyzed carboalumination chemistry (Wipf, Rapid Carboalumination of Alkynes in the Presence of Water, Agnew. Chem., Int. Ed. Engl., 32:1068–1071 (1993)) wherein a C16–C17 alkyne bond in an appropriately functionalized C13–C17 propargylic alcohol 16 (Scheme 6) is subjected to methylalumination in the presence of zirconocene dichloride ($Cp_2ZrCl_2$). The resultant alkenylalane is coupled with 2-methyl-4-bromothiazole 17 in the presence of zinc chloride under Pd(0) catalysis to access the trisubstituted E-olefin 19 stereoselectively following the protection of the alcohol 18 as the OTBS-ether.

The chiral propargylic alcohol 16 is obtained via the asymmetric reduction of the readily available alkynyl ketone 15. This is exemplified in Scheme 6, which illustrates the synthesis of the precursor for the naturally occurring epothilone. After the introduction of the thiazole moiety, the known primary alcohol 21 is revealed by deprotection of the PMB ether 19 and then oxidized to the previously reported (Mulzer, J., et al. *Easy Access to the Epothilone Family— Synthesis of Epothilone B*, Tetrahedron Lett., 39:8633–8636 (1998)), C13–C20 aldehyde 22.

Scheme 6

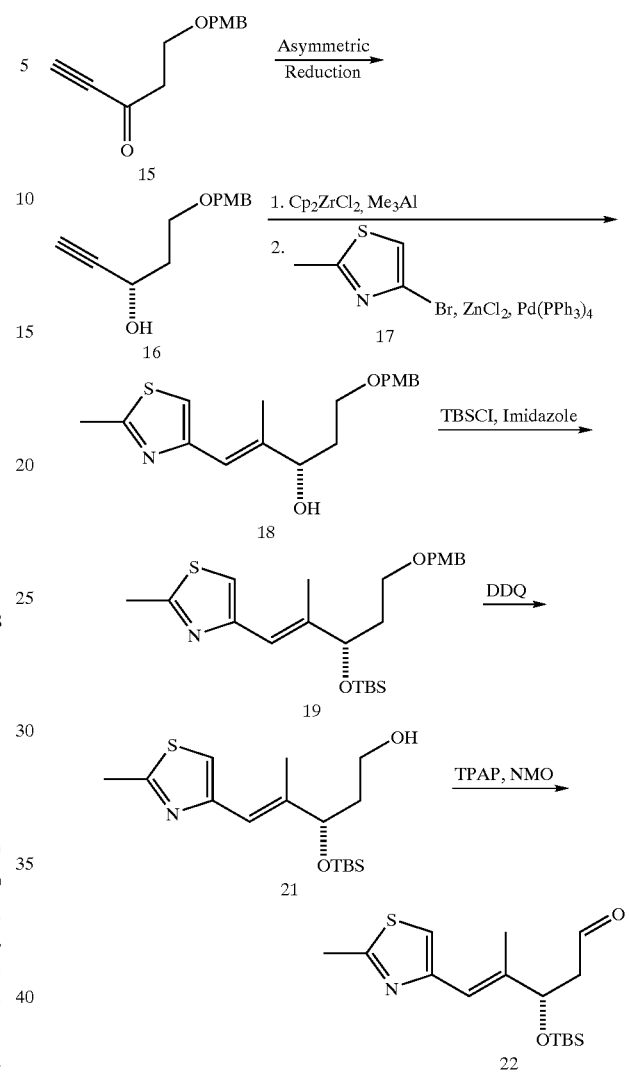

Alternately, a stannylcupration-methylation methodology (Harris, et al., *Synthetic Approaches to Rapamycin. 3. Synthesis of a C1–C21 Fragment*, Synlett, pp. 903–905 (1996)) can be used in order to introduce the trisubstituted olefin. Thus the O-TBS ether 16a (Scheme 7) of propargylic alcohol 16 on treatment with the stannylcuprate reagent 20 followed by methylation with iodomethane provides the corresponding stannane which is then coupled under Stille conditions with the bromothiazole 17 to yield the olefin 19.

Scheme 7

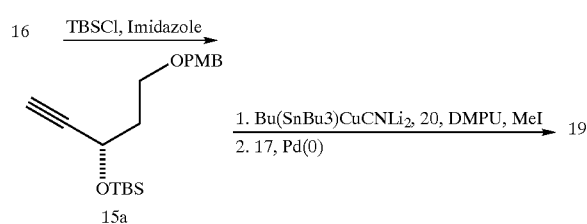

The synthesis of 2-methyl-4-bromothiazole 17 from the known 2,4-dibromothiazole (Reynaud, et al., *Sur une Nou-* velle Synthese du Cycle Thiazolique, Bull. Soc. Chim. Fr., 295:1735–1738(1962)) is outlined in Scheme 8.

Scheme 8

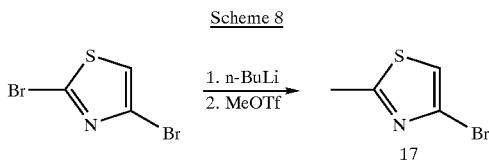

The zirconium-catalyzed methylalumination strategy constitutes a novel route to construct the C16–C17 double bond and to introduce the thiazole ring. The novelty lies in the use of a chiral propargylic alcohol like 16 in the carbometalation reaction followed by the direct introduction of the thiazole unit.

This methodology also allows for the introduction of various substituents and chain elongations on the C12–C20 segment A. Thus starting with analogs of the ketone 15 in Scheme 6, a variety of chain-elongated derivatives of segment A can be produced. Also carrying out an ethylalumination (Et$_3$Al) in place of methylalumination (AlMe$_3$) (Scheme 6) allows the introduction of an ethyl group (Et) at C16. In the same context, other groups can also be introduced using the alternate stannylcupration-alkylation method by replacing iodomethane with other electrophiles in this reaction shown in Scheme 7. In addition, the thiazole ring can be replaced by other cyclic, aromatic and heteroaromatic rings by using other vinyl or aromatic/heteroaromatic halides in place of 2-methyl-4-bromothiazole 17 in the coupling reaction following either the carboalumination or stannylcupration strategy exemplified in Schemes 6 and 7 respectively.

Stereoselective Construction of the C12–C13 cis-olefinic Bond of Formula A

The goals in the construction of the C12–C13 Z-olefinic bond, were to design a method providing maximum control over the olefin geometry and to furnish common intermediates in the synthesis of both epothilones A and B. The introduction of affinity labels at C-12 was also a consideration.

The C12–C13 olefin can be constructed in the form of Z-vinyl iodides I that can be obtained from vinylstannanes with defined configurations. The vinyl stannanes will be accessed by using known chemistry reported by Lipshutz et al., Preparation of Z-Vinylstannanes via Hydrozirconation of Stannylacetylenes, Tetrahedron Lett., 33:5861–5864 (1992); Lipshutz, et al., Hydrozirconation/Transmetalation of Acetylenic Stannanes. New 1,1-Dimetallo Reagents, Inorganica Chimica Acta, 220:41–44 (1994), which utilizes a 1,1-dimetallo species as a stereodefined 1,1-vinyl dianion synthon. An exemplary synthesis is given in Scheme 9, for the precursor to a naturally occurring epothilone, and starts with a Corey-Fuchs reaction (PPh$_3$, CBr$_4$) of the known aldehyde 22, followed by base-induced elimination and quenching of the lithium acetylide with tributyltin chloride (Bu$_3$SnCl) to yield alkynylstannane 23. The 1,1-dimetallo species 24 is generated by hydrozirconation of the alkynyl stannane 23 using chlorohydridozirconocene (Schwartz reagent). An aqueous quench would provide Z-vinylstannane 25a or alternatively, selective transmetalation with a higher order cuprate, followed by addition of an electrophile (MeOTf in case of epothilone B) to the resultant species provides the a-substituted vinylstannane 25b with high stereoselectivity. The Z-vinylstannanes 25a and 25b can then be transformed to the corresponding vinyl iodides I utilizing iodine with retention of configuration.

Scheme 9

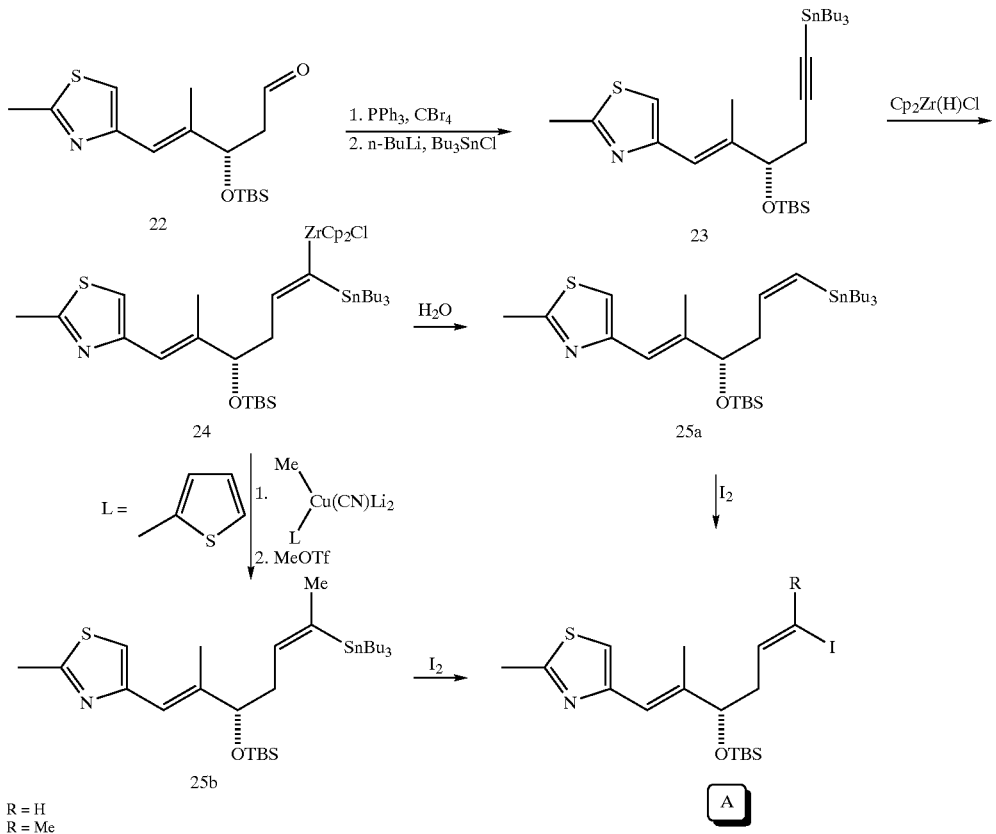

An alternative route to the synthesis of alkynylstannane 23 (Scheme 9a) which allows for incorporation of different substituents at the C16 carbon involves the asymmetric epoxidation of secondary alcohol 18a under the Sharpless conditions using (−)-diisopropyl tartrate, tert-butyl hydroperoxide and titanium isopropoxide to give epoxide 19a. The alcohol function on the epoxide can be oxidized with TPAP, NMO to give ketone 20a which can be reacted with Wittig reagents containing thiazole or other aromatic/heteroaromatic rings to give the corresponding trans-olefins. The terminal epoxide in this olefin can then be opened with trimethylsilyl acetylide to give secondary alcohol 22a. The trimethylsilyl group can then be substituted for a trialkyl stannyl group on treatment of 22a with TBAF and bis-tributyltin oxide and the obtained product treated with TBSCl to give compound 23.

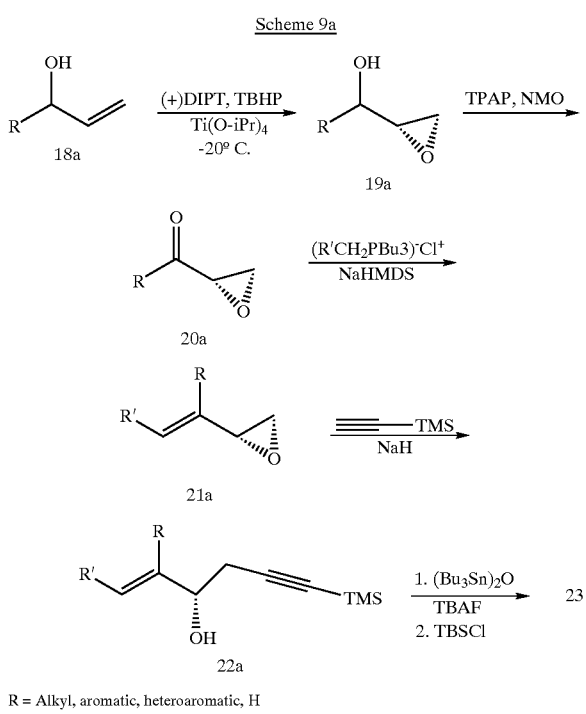

Scheme 9a

R = Alkyl, aromatic, heteroaromatic, H

The foregoing chemistries can be used for the synthesis of analog precursors as well. Such analogs are best illustrated by Formula X, wherein $n_3$, R, $R_1$ and $R_2$ are as defined previously. Again all of these modified segments can then be utilized in the total synthesis of various analogs of epothilones.

In summary, although some of the vinyl iodides of the Formula X are previously reported (20,21) compounds, the method to synthesize it from the known aldehyde 22 is different from conditions reported in other total syntheses of epothilones. In addition, the above mentioned hydrozirconation reactions provide precise control over the geometry of the C12–C13 olefin bond. Also the use of other electrophiles in the transmetalation reaction with the intermediate species 24 allows for the synthesis of various analogs.

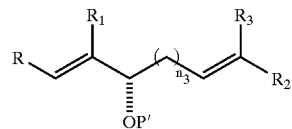

The invention also provides new synthetic routes to specific preferred embodiments of the above Formula X defined previously, in particular C12–C20 vinyl halide epothilone precursors of the formula.

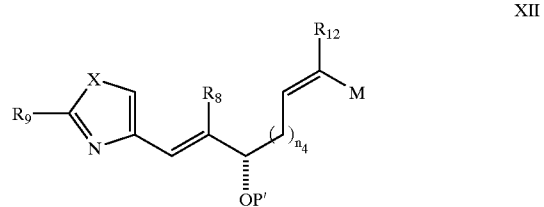

A preferred reaction Scheme 9B set forth below illustrates this aspect of the invention. Thus, the known aldehyde 1 was treated with the phosphonate 2 in presence of barium hydroxide and wet tetrahydrofuran as solvent to give the enone 3 in 75% yield. The asymmetric reduction of this enone 3 using 50 mol % of commercially available chiral catalyst (R)-2-Me-CBS-oxazaborolidine and 1.5 equivalents of borane dimethylsulfide complex in dichloromethane gave the desired alcohol 4 in 79% yield and in 95% enantiomeric excess. The completion of the segment synthesis involved the protection of the C15 alcohol as the TBS ether to provide the known compound 5 using TBSOTf (tert-butyldimethylsilyl trifluoromethanesulfonate) and 2,6-lutidine as base. The remaining steps (i.e.conversion of 5 to I) to the known vinyl iodide I have been previously reported in literature.

Scheme 9B

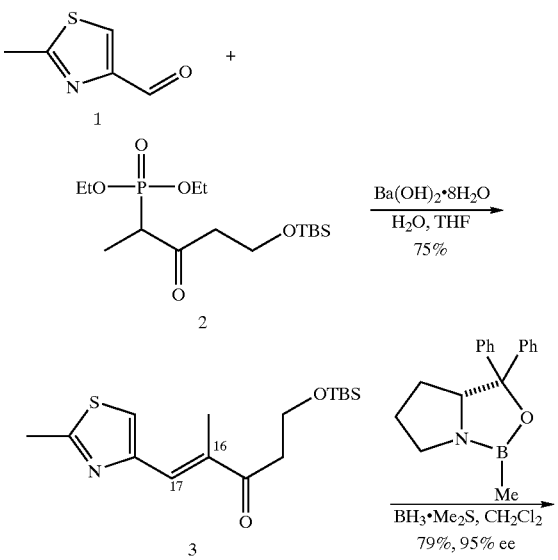

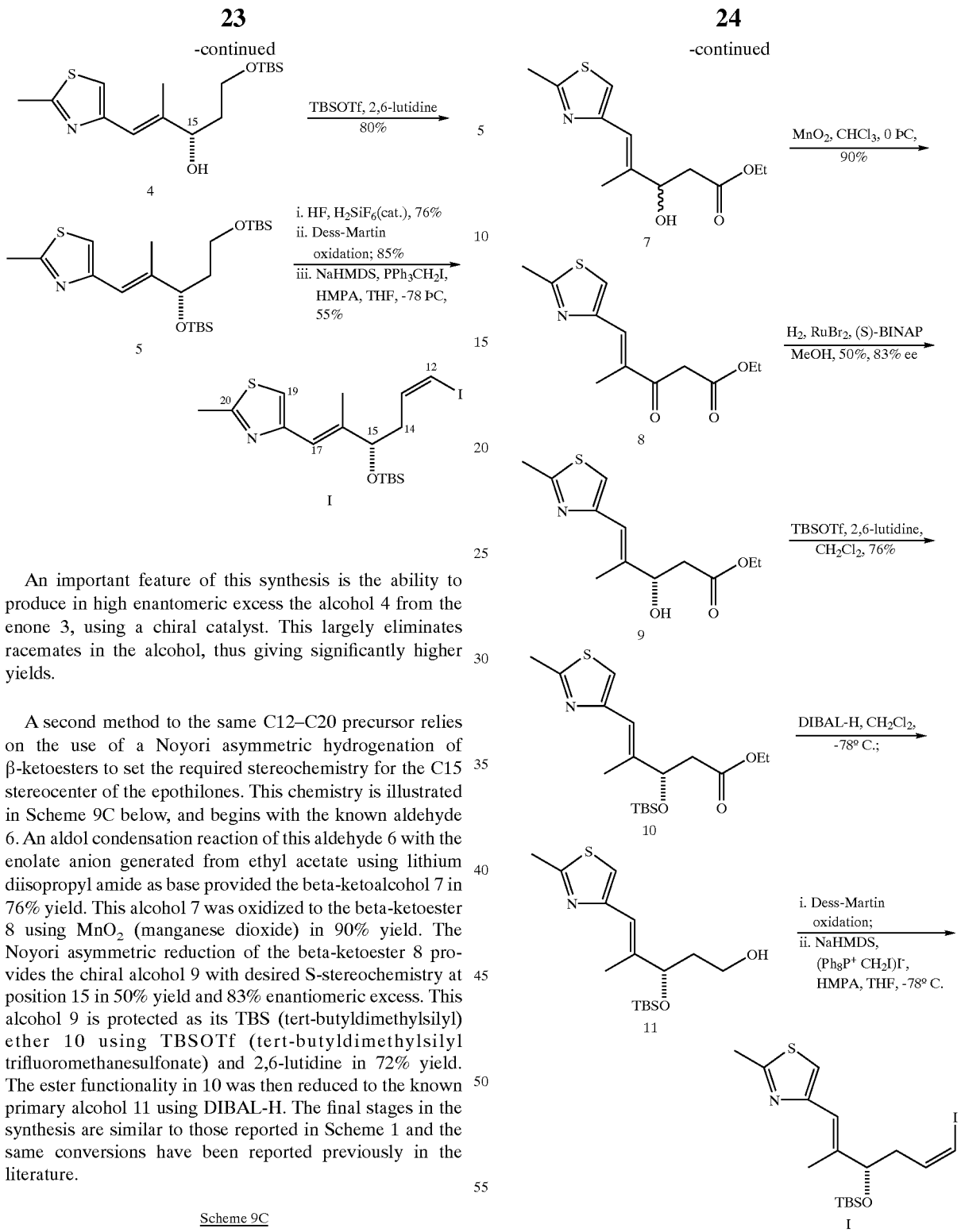

An important feature of this synthesis is the ability to produce in high enantiomeric excess the alcohol 4 from the enone 3, using a chiral catalyst. This largely eliminates racemates in the alcohol, thus giving significantly higher yields.

A second method to the same C12–C20 precursor relies on the use of a Noyori asymmetric hydrogenation of β-ketoesters to set the required stereochemistry for the C15 stereocenter of the epothilones. This chemistry is illustrated in Scheme 9C below, and begins with the known aldehyde 6. An aldol condensation reaction of this aldehyde 6 with the enolate anion generated from ethyl acetate using lithium diisopropyl amide as base provided the beta-ketoalcohol 7 in 76% yield. This alcohol 7 was oxidized to the beta-ketoester 8 using $MnO_2$ (manganese dioxide) in 90% yield. The Noyori asymmetric reduction of the beta-ketoester 8 provides the chiral alcohol 9 with desired S-stereochemistry at position 15 in 50% yield and 83% enantiomeric excess. This alcohol 9 is protected as its TBS (tert-butyldimethylsilyl) ether 10 using TBSOTf (tert-butyldimethylsilyl trifluoromethanesulfonate) and 2,6-lutidine in 72% yield. The ester functionality in 10 was then reduced to the known primary alcohol 11 using DIBAL-H. The final stages in the synthesis are similar to those reported in Scheme 1 and the same conversions have been reported previously in the literature.

Scheme 9C

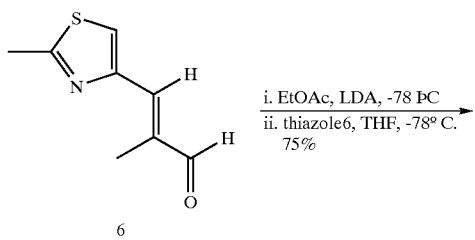

Two other epothilone derivatives of special interest maybe synthesized in accordance with the invention. In one such derivative the lactone functional group is replaced with an ether functionality and in the other a lactam functionality is used in lieu of the lactone functional group. Thus in the first derivative, and referring to Formula A, X is O, Y is $H_2$, $n_1$, $n_2$, and $n_3$ are 1, R is 2-methyl-thiazol-4-yl, $R_1$ is methyl, $R_2$ is H or methyl, and $R_3$, $R_4$, $R_5$ and $R_6$ are methyl. In the second derivative, the only change is that X is NH and Y is O. These could be synthesized by the reaction sequences shown in Schemes 10 and 11. Thus selective deprotection at C1 by camphorsulfonic acid (CSA) (Scheme 10), formation of the mesylate derivative of the corresponding primary alcohol, selective deprotection of the C15 TBS ether and base-induced cyclic ether formation should provide compounds 26'. Again, the final stages in the synthesis would involve the deprotection of both the TBS groups from the macrolides (TFA, $CH_2Cl_2$) and the diastereoselective epoxidation of the C12–C13 double bond with epoxidizing agents such as dimethyldioxirane to give the ether derivatives 29 and 30.

For the lactam formation (Scheme 11) again compound 26 could be selectively deprotected at C-1 followed by sequential oxidation of the primary alcohol first under Swern conditions followed by $NaClO_2$—$NaH_2PO_4$ would furnish the known acids. These known acids can be converted to their allyl esters and then the TBS ether at C15 can be deprotected selectively. Mitsunobu inversion of these alcohols and azide formation via the corresponding mesylates will provide the azides with the correct stereochemistry at C15. Reduction of the azides ($PPh_3$, $H_2O$) followed by salt formation of the amine will provide 32. Deprotection of the allyl esters ($Pd(PPh_3)_4$, base) followed by macrolactamization (HBTU) will provide the lactams 33. Again, deprotection of both the TBS groups from the macrolides (TFA, $CH_2Cl_2$) and the diastereoselective epoxidation of the C12–C13 double bond with epoxidizing agents such as dimethyldioxirane would give the lactam derivatives 34 and 35.

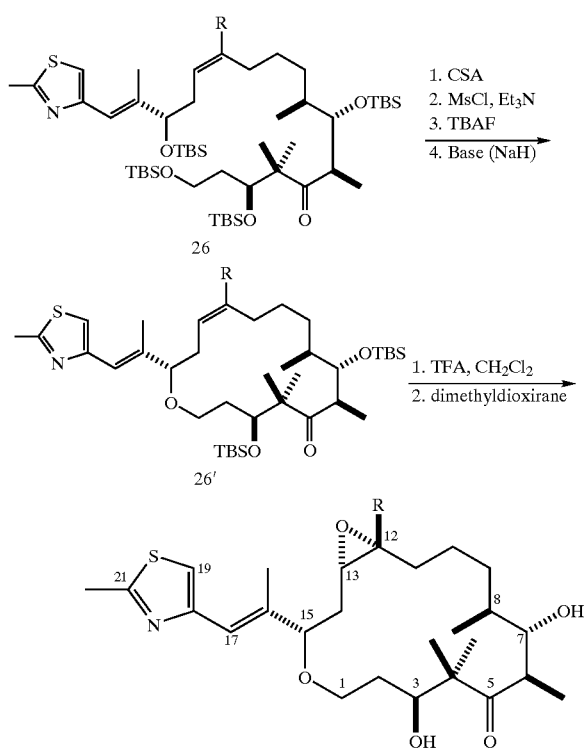

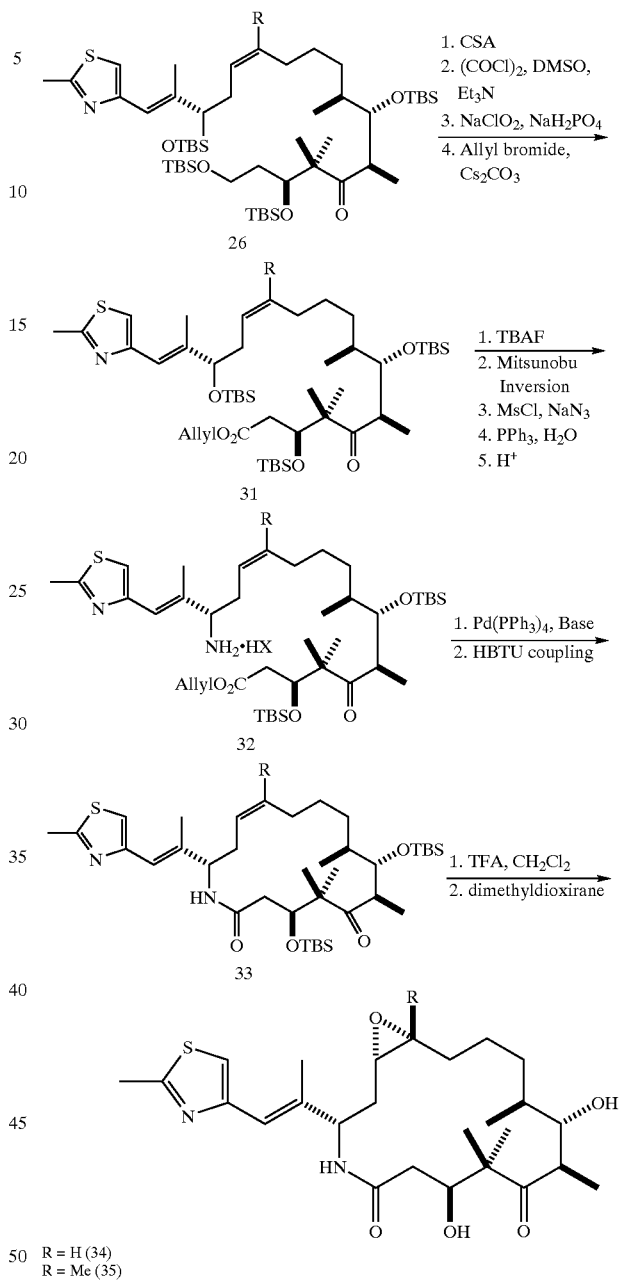

Representative C4–C8 cycloalkyl, substituted and unsubstituted aromatic and heteroaromatic groups, C1–C10 straight and branched chain alkyl groups, substituted and unsubstituted benzyl groups, C1–C10 alkoxy groups, and heterocyclic groups useful in the formation of epothilone analogs are set forth below.

C4–C8 cycloalkyl groups: cyclobutyl, cyclopentyl, cyclohexyl, cycloheptyl, cyclooctyl.

Substituted and unsubstituted aromatic groups: phenyl, phenyl groups substituted at any position with C1–C4 straight or branched chain alkyls, C1–C4 alkoxy groups, halogens, amines, amides, azides, sulfides, carboxylic acids and their derivatives, and hydroxides.

Substituted and unsubstituted heteroaromatic groups: thiazoles, pyrroles, furans, thiophenes, oxazoles and pyridines, and imidazoles.

C1–C10 straight and branched chain alkyl groups: methyl, ethyl, propyl, butyl, isopropyl, isobutyl, isopentyl, octyl, nonyl, and t-butyl.

Substituted and unsubstituted benzyl groups: benzyl, benzyl groups substituted at any position with C1–C4 straight or branched chain alkyls, C1–C4 alkoxy groups, halogens, amines, amides, azides, sulfides, carboxylic acids and their derivatives, and hydroxides.

C1–C10 alkoxy groups: methoxy, ethoxy, propoxy, butoxy, isopropoxy, t-butoxy, and nonoxy.

Heterocyclic groups: piperidines, furans, pyrroles, oxazolines, and thiophenes.

The following examples set forth various syntheses of the type described previously. It is to be understood, however, that these examples are provided by way of illustration and nothing therein should be taken as a limitation upon the overall scope of the invention.

EXAMPLE 1

The synthesis of a segment C precursor was accomplished via two unique and complementary routes which are detailed in Schemes 2 and 3. One novel step in the synthesis of the C1–C6 segment utilizes the Noyori hydrogenation as detailed in Noyori, R. et al., *Asymmetric Hydrogenation of β-Keto Carboxylic Esters. A Practical, Purely Chemical Access to β-HydroxyEsters in High Enantiomeric Excess*, J.Am. Chem. Soc., 109:5856–5858 (1987). The Noyori hydrogenation of β-keto ester 4 in Scheme 2 generates the requisite stereochemistry at C3. This Noyori hydrogenation provides the required enantiomer with high selectivities (95% enantiomeric excess). It is a versatile reaction and has found numerous applications in the synthesis of biologically active natural products and is also amenable to large scale synthesis.

The following is a detail of the procedures that are outlined in Scheme 2. The required β-keto ester 4 is obtained in two steps from the readily available starting material 3-benzyloxypropionic acid (2) as described by Davis et al., *Nonracemic α-fluoro aldehydes: Asymmetric synthesis of 4-deoxy-4-fluoro-d-arabinopyranose*, J. Org. Chem., 62:7546–7547 (1997), the teachings of which are hereby incorporated by reference. Isopropylcyclohexyl-amine (7.3 mL, 44.6 mmol, 1.5 eq.) was dissolved in 40 mL THF. The temperature was then lowered to −30° C. and n-butyllithium (16.1 mL, 38.6 mmol, 1.3 eq.) was added dropwise and stirred for 30 minutes. Next, the temperature was raised to 0° C. for 15 minutes and then cooled to −78° C. for 15 minutes. Methyl isobutyrate (3.75 mL 32.7 mmol, 1.1 eq.) was dissolved in 5 mL THF and added dropwise. The resulting mixture was stirred 30 minutes. 3-Benzyloxypropionyl chloride (5.0 g, 29.7 mmol, 1 eq) in 5 mL THF was then added dropwise. This reaction mixture was stirred for one hour until the starting material completely disappears by thin layer chromatography (TLC) (80:20 hexanes/EtOAc). The reaction mixture was then quenched with 20 mL 20% HCl and raised to room temperature. Next, the reaction mixture was extracted 3 times with ether and the combined organic phases were washed twice with sodium bicarbonate and once with brine. The combined aqueous layers were cross-extracted twice with ether. The organics were combined, dried with $Na_2SO_4$, and concentrated under reduced pressure. Purification was achieved via column chromatography on silica gel using a hexane/EtOAc gradient which resulted in 5.1 g (65% yield) of β-keto ester 4.

Asymmetric hydrogenation of β-keto ester 4 in methanol using $RuBr_2(S)$-binap as catalyst at 65 psi gave the β-hydroxyester 5 in 85% yield. This was done by the following process. Acetone and MeOH were distilled and stored over molecular sieves. Each was degassed five times using the freeze-thaw method and placed under argon. Noyori's ruthenium catalyst (91 mg, 0.284 mmol, 1 eq.), preferably bis-(2-methylallyl)cycloocta-1.5-diene ruthenium (II) and (S)-BINAP (S)-(−)-1,1'bi-2-naphthal(s)-(−)-2, 2'-Bis (diphenylphosphino)1,1'binaphthyl (177 mg, 0.284 mmol, 1 eq.) were combined in a Schlenk flask with 24 mL acetone and 2.0 mL HBr solution (0.25 mL 48% HBr, 5.1 mL acetone). The resulting mixture was stirred for 4 hours to allow the catalyst to form. The acetone was then removed under reduced pressure. Next, beta ketoester 4 (5.36 g, 20.3 mmol, 71.5 eq.) in 23 mL MeOH was degassed four times and then transferred to a Parr hydrogenation flask using MeOH. The catalyst was then rinsed into the Parr flask using MeOH. The hydrogenation reaction was conducted over 110 hours at 65 psi and 60° C. The contents were concentrated under reduced pressure and then taken up in ether. The reaction mixture was filtered twice to remove the catalyst and then concentrated. Final purification was obtained through column chromatography wherein the column contained silica gel and utilized a hexane/EtOAc gradient and yielded 4.57 g (85% yield).

Deprotection of the benzyl ether and bis-silylation of diol 6 provided ester 7. To produce diol 6, β-hydroxyester 5 (1.824 g, 6.86 mmol, 1 eq.) was dissolved in 20 mL THF and transferred to a Parr hydrogenation vessel under argon. $Pd(OH)_2$ (450 mg, 0.25 eq.) was added and the flask purged for an additional 10 minutes with argon. The hydrogenation reaction was conducted at 50 psi for 24 hours. Finally, the reaction mixture was washed through a frit, an ultrafine strainer in a filtration technique preferably fit with 300 mL EtOAc and concentrated under reduced pressure to give 1.18 g (90% yield) of diol 6.

In detail, ester 7 was made by taking diol 6 (450 mg, 2.84 mmol, 1 eq) dissolved in 3.15 mL DMF and adding imidazole (1.16 g, 17.04 mmol, 6 eq) which was stirred until dissolved. TBSCl (tert-Butyldimethylsilyl chloride) (1.28 g, 8.52 mmol, 3 eq) was added and the temperature was raised to 60° C. This reaction mixture was then stirred for 44 hours. Disappearance of the starting material was monitored by thin layer chromatography. The reaction was then quenched with $H_2O$ and $NH_4Cl$. After quenching, the reaction mixture was extracted twice with ether. The ether layer was washed with $NaHCO_3$ and brine, dried with $Na_2SO_4$, and concentrated. Purification via column chromatography ($SiO_2$, 95:5 hexane/EtOAC) gave 0.89 g or a 78% yield.

Primary alcohol 8 is the result of reducing ester 7 (1.89 g, 4.68 mmol, 1 eq) by dissolving it in 26 mL of $CH_2Cl_2$, cooling it to −78° C. and adding DIBAL-H (9.4 mL, 14 mmol, 1.5M in hexanes) dropwise. After stirring at this temperature (−78 ° C.) for one hour, the reaction was quenched with 10 mL of MeOH. Next, the reaction mixture was warmed to 0° C. and 10 mL of a saturated aqueous solution of potassium sodium tartarate was added. After stirring this mixture for 16 hours, the aqueous layer was extracted four times with $CH_2Cl_2$. The combined organics were dried over anhydrous sodium sulfate and concentrated to yield 1.59 g (92% yield) of the primary alcohol. Although this is a known alcohol, the synthetic route from this ester is novel.

Primary alcohol 8 was oxidized to aldehyde 9 by taking primary alcohol 8 (1.45 g, 3.86 mmol, 1 eq) and dissolving it in 25 mL $CH_2Cl_2$. Molecular sieves (4 Å, powdered) were added to aid in the removal of water and this mixture was stirred for 15 minutes. 4-methylmorpholine N-oxide (NMO)

(0.77 g, 6.56 mmol, 1.7 eq) was then added and after stirring for 30 minutes, tetrapropylammonium perruthenate (TPAP) (0.081 g, 0.23 mmol, 0.06 eq) was added. The reaction mixture was stirred for 16 hours at room temperature and then concentrated. It was then passed through a pad of 4:1 silica gel:Celite mixture (35 g) to yield 1.2 g (83% yield) of the aldehyde.

The aldehyde 9 is then reacted with EtMgBr using the procedure of Claus, E. et al., *Synthesis of the C1–C9 Segment of Epothilons*, 38 Tetrahedron Lett., 1359–1362 (1997), the procedure of which is hereby incorporated by reference, to give the known secondary alcohol 10 in 65% yield.

This secondary alcohol 10 is then oxidized to the C1–C6 segment C using the same procedure that was used to oxidize primary alcohol 8 to aldehyde 9. The alcohol 10 (50 mg, 0.124 mmol, 1 eq) was dissolved in 1 mL $CH_2Cl_2$. Molecular sieves (4 Å, powdered) were added and this mixture was stirred for 15 minutes. NMO (25 g, 0.211 mmol, 1.7 eq) was then added and after stirring for 30 minutes, TPAP (3 mg, 0.0074 mmol, 0.06 eq) was added. The reaction mixture was stirred for 15 hours at room temperature and then concentrated. It was then purified bypassing it through a column (20 g) of 5:1 silica gel:Celite mixture (5% EtOAC in hexane) to yield 46 mg (92%) of the ketone (segment C). Again although segment C is known the oxidation process used is different from conditions reported.

In summary, although segment C is a key synthon in previously reported total syntheses of the epothilones, the synthetic route utilizing the asymmetric Noyori hydrogenation is unique.

EXAMPLE 2

Scheme 3 outlines an alternate synthesis of β-hydroxyester 5 using known compound 13. This alternate route toward the segment C precursor allows for the introduction of affinity labels and modifications at the C4 position as shown in Scheme 3. Applying the Noyori reduction to the known unsubstituted β-keto ester 11 provides a building block that can be used for the modifications at C4 of the epothilones. There has only been one report so far of C4 modification on the epothilones and this method provides a more general route of introducing a variety of substituents at this position. This will also enable a more thorough study of the structure activity relationships of numerous C4 substituted analogs.

Thus, the Noyori hydrogenation of β-keto ester 11 yields the known β-hydroxyester 12, which was reported by Ali, et. al, *Formal Syntheses of Cryptophycin 1 and Arenastatin A.,* 38 Tetrahedron Lett., 1703–1706 (1997), hereby incorporated by reference, in 97% yield (in 97% enantiomeric excess). The Frater alkylation of β-hydroxy ester 12 yields the previously reported a-methyl analog 13 also previously reported by Ali et al. *Formal Syntheses of Cryptophycin 1 and Arenastatin A.,* 38 Tetrahedron Lett., 1703–1706 (1997), hereby incorporated by reference, in 71% yield (98% diastereomeric excess). A second Frater alkylation of hydroxy ester 13 gave bis-dimethyl derivative 5 in 59% yield which was then converted to epothilone segment C by the chemistry shown in Scheme 2.

In detail, isopropylcyclohexylamine (0.71 L, 4.32 mmol, 2.16 eq.) and 3.75 mL THF were stirred together at −25° C. n-BuLi (1.64 mL, 3.6 mmol, 1.8 eq.) was added dropwise over 15 minutes. The reaction mixture was stirred at room temperature for 15 minutes and then lowered to −78° C. Compound 13 (504 mg, 2 mmol, 1 eq.) in 2.5 mL THF was added to the reaction mixture. The temperature was gradually raised to −10° C. over 4 hours and then returned to −78° C. MeI (0.17 mL, 2.66 mmol, 1.33 eq.) in HMPA (0.26 mL) was added dropwise. The reaction was stirred at −78° C. for one hour and then stirred at room temperature for 16 hours. The reaction was quenched with 4 mL 10% HCl . The mixture was then extracted four times with $CH_2Cl_2$, dried over $Na_2SO_4$, and concentrated. Purification by column chromatography 160 g $SiO_2$ (hexane/EtOAc gradient) gave 312 mg (a 59% yield) of β-hydroxyester 5.

At this stage, other substituents such as benzyl, allyl and other alkyl groups can be introduced by using other electrophiles in the second Frater alkylation in place of iodomethane. The novel aspect about this alternate route to segment C is the ability to alter the substituents at the C4 position of the epothilones using the aforementioned Frater alkylation strategy. After synthesis of β-hydroxyester 5, the segment C can be produced following the procedure outlined above in Scheme 2.

It should be noted that this invention makes it possible to synthesize several analogs of this C1–C6 segment with various chain elongations at C2 and substitution at C6 positions on the epothilones. It also allows for, as mentioned before, modifications at the C4 position with other groups such as aryl, heterocyclic, alkyl and branched alkyl. These chain extensions and substitutions are illustrated by Formula C. The synthesis of these modified derivatives can be achieved utilizing chemistry exemplified in the synthesis of segment C in Schemes 2 and 3 respectively. These modified segments can then be utilized in the total synthesis of various analogs of epothilones.

EXAMPLE 2A

The following sets forth a preferred procedure for synthesis of a specific C1–C6 segment C precursor using the chemistry of Scheme 3A above.

Synthesis of Diol 13

Ethyl-(R)-4-cyano-3-hydroxybutanoate 12 (0.100 g, 0.637 mmol) was dissolved in ethanol (10 mL) and the temperature was lowered to 0° C. Sodium borohydride (0.024 g, 0.637 mmol 1.00 equiv) was added to the flask and the reaction was stirred for 2 hours. An additional equivalent of $NaBH_4$ was added after 2 hours, and a third equivalent after 2 more hours. The reaction was gradually warmed to room temperature and allowed to stir overnight. The temperature was returned to 0° C. and the reaction was quenched with a 25% acetic acid solution in ethanol. After stirring for one hour, the solvents were evaporated and the residual white solid was filtered over a cotton plug with EtOAc washing. The crude product was concentrated and dried overnight on high vacuum and carried forward to the next reaction without further purification.

Synthesis of β-hydroxynitrile 14

To diol 13 (0.02 gm, 0.174 mmol) taken in a 50 mL flask, 40 mL of dry benzene was added followed by (0.043 mL, 0.191 mmol) dibutyltin dimethoxide and the solution heated to reflux under argon in an oil bath with a Dean-Stark apparatus. After about 25 mL of benzene distilled over into the sidearm, the solution was cooled and p-methoxy benzyl chloride (0.029 gm, 0.191 mmol) and tetrabutylammonium iodide (0.096 gm, 0.26 mmol) were added. After stirring at room temperature overnight the reaction mixture was stirred at 60° C. for 4 hours. Cooling to room temperature followed by addition of aqueous ammonium chloride and extraction with ethyl acetate gave the crude product. Column chromatography with 35% EtOAc/Hexanes gave 25 mg of product 14 (61% yield).

Synthesis of Dimethyl-hydroxynitrile 15

Diisopropylamine (0.107 mL, 0.766 mmol) was added to 5 mL of dry THF and the solution under argon was cooled to −78° C. in a dry ice bath with stirring. n-butyl lithium (0.51 mL, 0.71 mmol, 1.4M) was added and the solution allowed to rise to room temperature. The solution was stirred for 15 minutes at room temperature and cooled again to −40° C. and the β-hydroxynitrile 14 (0.04 g, 0.17 mmol) was added and gradually warmed. After the solution reached room temperature, the mixture was brought to reflux using a water bath at 60° C. for 15 minutes and then 0.15 mL (excess) of methyl iodide was added. The yellowish solution turned to a white slurry in a few minutes. After 15 minutes saturated ammonium chloride was added, the aqueous layer separated and extracted thrice with EtOAc (25 mL), dried over $Na_2SO_4$ and concentrated. Column chromatography with 15% EtOAc/hexane gave 0.034 g (76% yield) of 15.

Synthesis of Ketone 16

Nitrile 15 was (0.04 gm, 0.15 mmol) dissolved in 2 mL of dry THF under argon and stirred as EtMgBr (0.2 mL, 0.456 mmol) was added. About 5 mg (catalytic amount) of $CuBr.Me_2S$ was added and the solution was refluxed for 24 hours. After cooling to room temperature, a 0.06 M solution of aqueous citric acid was added to the reaction mixture and stirring continued for 5 hrs. The solution was then extracted five times with EtOAc (40 mL). The combined organic layers were washed with saturated $NaHCO_3$ and brine, dried over $Na_2SO_4$ and concentrated. Column chromatography with 15% EtOAc/hexanes gave 25 mg (56% yield) of ketone 16.

Synthesis of Diol 17

To compound 16 (0.064 gm, 0.217 mmol) dissolved in 9 mL of acetonitrile and 1 mL of water (0.357 gm, 0.652 mmol) 3 equivalents of ceric ammonium nitrate was added as the reaction mixture was stirred in an ice bath. The reaction mixture was allowed to warm to room temperature and stir for 3 hours. Solid sodium bicarbonate 0.25 gm was added followed by 0.25 gms of $Na_2SO_3$ and stirring continued overnight. All solvents were evaporated and the solid residue filtered and washed with ethyl acetate (50 mL), dried over $Na_2SO_4$ and concentrated. The crude product obtained was purified by column chromatography to give 26 mg, 70% yield of diol.

Synthesis of Ketone 18

To diol 17 (0.026 gm, 0.15 mmol) dissolved in 4mL of dry DCM, 2,6-lutidine (0.154 mL, 7.0 equivalents) followed by TBSOTf (0.205 ml, 6 equivalents) were added as the reaction mixture was stirred in an ice bath. The reaction was stirred overnight and 10 mL of $NH_4Cl$ was added followed by 20 mL of $CHCl_3$. The organic layer was separated and the aqueous layer was extracted five times, each with 25 mL of $CHCl_3$, dried over $Na_2SO_4$ and concentrated. Column chromatography with 2% ethyl acetate gave 34 mg (65% yield) of product 18.

EXAMPLE 2B

This example sets forth a synthesis in accordance with Scheme 2B. The steps leading to ester 25 are specified in Scheme 2B and are similar to the steps of Schemes 3 and 2 and the supporting examples. However, the preferred synthesis from compound 25 to 26 is set forth below.

Improved Synthesis for Ketone 26

Ethyl phenyl sulfone (3.4 g, 20 mmol, 5.5 equiv) was dissolved in THF (50 mL) and the temperature was lowered to −78° C. n-BuLi (13 mL, 18 mmol, 5.0 equiv) was added dropwise to the sulfone and a pale yellow solution formed which was stirred at −78° C. for 1.5 hours. The ester in THF (15 mL) was added dropwise at −78° C. to the solution containing compound 25. The bath was removed and the reaction stirred at room temperature for 20 hours. The reaction was quenched with 1:1 saturated $NH_4Cl$ and water (30 mL) and the aqueous layer was extracted five times with $Et_2O$. The organic layer was dried over $Na_2SO_4$ and concentrated. The crude was then dissolved in MeOH (50 mL) and then the temperature was lowered to 0° C. $NaH_2PO_4$ (2.00 g, 14.4 mmol, 4.00 equiv) was added followed by Na(Hg) (4.39 g). The pink suspension which developed was stirred at 0° C. for 1 hour and 15 minutes, and 1:1 saturated $NH_4Cl$ and water were added followed by dilution with $Et_2O$. The mercury metal was filtered using a funnel and a plug of glass wool. The filtrate was extracted five times with $Et_2O$. The combined organic layer was washed with $H_2O$ and brine, dried over $Na_2SO4$ and concentrated. Flash column chromatography using 5% $Et_2O$ in hexane provided 1.3 g (90%) of the ketone.

EXAMPLE 3

This example illustrates the synthesis of segment B as in Scheme 4. The synthesis of the C7–C11 segment B has been achieved using previously reported chemistry of Lin, et al., *Efficient Total Syntheses of Pumiliotoxins A and B. Applications of Iodide-Promoted Iminium Ion-Alkyne Cyclization in Alkaloid Construction* 118 J. Am. Chem. Soc., 9062–9072 (1996), the teachings of which are hereby incorporated by reference, and is outlined in Scheme 4. This synthesis can also be used to introduce various chain-elongations on this segment and to introduce various other substituents at C-8. These modifications can be illustrated by Formula IX and their synthesis can be achieved using chemistry exemplified in the synthesis of segment B in Scheme 4. Again, these modified segments can then be utilized in the total synthesis of various analogs of epothilones.

EXAMPLE 4

This example, illustrated in Scheme 5, describes the synthesis of aldol adduct 14 followed by the aldol reaction of the segment C precursor, from examples 1 or 2, with segment B, from example 3. Aldol adduct 14 was then used to synthesize segment D of Scheme 5.

The connection of the two segments C and B utilizes a highly diastereoselective aldol reaction (Scheme 5). When the C1–C6 ketone segment C was treated with a base, namely lithium diisopropylamide and the resultant enolate reacted with C7–C11 aldehyde segment B a single diastereomer 14 was observed in 65% yield. The remarkable diastereoselectivity is speculated to arise from a favorable nonbonding interaction between the C10–C11 double bond and the carbonyl group of the aldehyde that gives rise to the desired diastereomer. This connection between these two particular segments using an aldol reaction is unprecedented. After the connection has been made, the resultant secondary alcohol will be protected as the corresponding tert-butyldimethylsilyl ether D.

In detail, diisopropylamine (60 μL, 0.45 mmol, 1 eq) dissolved in 1 mL THF was cooled to −78° C. and n-BuLi (0.33 mL, 0.43 mmol, 0.95 eq) was added dropwise. After stirring at −78° C. for 15 minutes and at 0° C. for 30 minutes the reaction mixture was recooled to −78° C. The ketone (segment C) (0.184 g, 0.45 mmol, 1 eq) dissolved in 1 mL of THF was then added dropwise. This mixture was stirred at −78° C. for 15 minutes and then warmed to −40° C. over one hour. After recooling to −78° C., the aldehyde segment B (0.022 g, 0.23 mmol, 0.5 eq) dissolved in 0.5 mL $Et_2O$ was added dropwise over 15 minutes. After 35 minutes at −78° C., the reaction was quenched with 2 mL saturated aqueous ammonium chloride and warmed to room temperature. The aqueous layer was extracted five times with $Et_2O$ and the combined organics were dried over anhydrous magnesium sulfate. After concentration, preparative thin layer chromatography of the residue yielded 0.047 g (21% yield) of the desired diastereomer.

Forming segment D utilizes TBS protection of adduct 14. Aldol adduct 14 (30 mg, 0.06 mmol, 1 eq.) was diluted with 1.5 mL $CH_2Cl_2$ and the temperature was lowered to −78° C. 2,6-lutidine (50 μL, 0.42 mmol, 7 eq.) was added dropwise followed by tert-butyl-dimethylsilyl trifluoromethanesulfonate (TBSOTf) (70 μL, 0.30 mmol, 5 eq.). The reaction was stirred for 15 minutes and then raised to 0° C. The reaction was complete after 3 hours and was quenched with 5 mL $NH_4Cl$. The mixture was extracted three times with $CH_2Cl_2$ and the combined organic layers were washed with brine, dried over $MgSO_4$ and then concentrated. Column chromatography (5% EtOAc in hexane) gave 34 mg (96% yield) of compound D.

EXAMPLE 5

This example illustrates the synthesis of a segment A precursor (the C-12–C-20 segment) and is outlined in Scheme 6. This involves new ways to set the C16–C17 trisubstituted double bond and the C12–C13 cis-double bond which serves as precursor to the cis-epoxide at C12–C13 in the epothilones. The methodology used to introduce the thiazole moiety draws upon zirconium-catalyzed carboalumination chemistry as described by Wipf, P. and Lim, S., *Rapid Carboalumination of Alkynes in the Presence of Water,* 32 Agnew. Chem., Int. Ed. Engl., 1068–1071 (1993), the teachings of which are hereby incorporated by reference. Using this chemistry, a C16–C17 alkyne bond in an appropriately functionalized C13–C17 propargylic alcohol 16 is subjected to methylalumination in the presence of zirconocene dichloride ($Cp_2ZrCl_2$). The chiral propargylic alcohol 16 is obtained via the asymmetric reduction of the readily available alkynyl ketone 15. A number of methods have been developed during the past years for the enantioselective reduction of α,β-alkynyl ketones. The resultant alkenylalane is coupled with 2-methyl-4-bromothiazole 17 in the presence of zinc chloride under Pd(0) catalysis as described by Negishi, E.-I., et al., in *Double Metal Catalysis in the Cross-Coupling Reaction and Its Application to Stereo-and Regioselective Synthesis of Trisubstituted Olefins,* J. Am. Chem. Soc., 100:2254–2256 (1978) and Negishi, E.-I., in *Palladium-or Nickel-Catalyzed Cross Coupling. A New Selective Method for Carbon-Carbon Bond Formation,* Acc. Chem. Res., 15:340–348 (1982), the teachings of which are hereby incorporated by reference. Scheme 8 illustrates the synthesis of 2-methyl-4-bromothiazole 17 which was synthesized by adding 9.0 mL ether and n-BuLi (1.8 mL, 2.96 mmol, 1.2 eq) and stirring at −78° C. for 30 minutes. The bromothiazole (0.60 g, 2.47 mirol, 1 eq.) in 3.5 mL of ether was added dropwise to the n-BuLi. After stirring for one hour, MeOTf (0.56 mL, 4.94 mmol, 2 eq.) was added dropwise and the reaction mixture was stirred for an additional 1.5 hours. The reaction was then quenched with $NaHCO_3$ and extracted 5 times with ether. The combined organic layers were washed with brine, dried over $Na_2SO_4$, and concentrated. 262 mg (60% yield) of the 2-methyl-4-bromothiazole 17 was obtained and carried on without further purification.

This coupling of the alkenylalane to 2-methyl-4-bromothiazole 17 permits access to the trisubstituted E-olefin 19 stereoselectively following the protection of the alcohol 18 as the OTBS-ether.

After the introduction of the thiazole moiety, the known primary alcohol 21(Mulzer et al., *Easy Access to the Epothilone Family—Synthesis of Epothilone B,* Tetrahedron Lett., 39:8633–8636 (1998) is revealed by deprotection of the PMB ether 19 and then oxidized to C13–C20 aldehyde 22, also previously reported by Mulzer, et al., *Easy Access to the Epothilone Family—Synthesis of Epothilone B,* Tetrahedron Lett., 39:8633–8636 (1998), the teachings of which are hereby incorporated by reference.

The zirconium-catalyzed methylalumination strategy constitutes a novel route of constructing the C16–C17 double bond and introduction of the thiazole ring. The novelty lies in the unprecedented use of a chiral propargylic alcohol like 16 in the carbometalation reaction followed by the direct introduction of the thiazole unit.

This methodology also allows for the introduction of various substituents and chain elongations on the C12–C20 segment A. Thus starting with analogs of the ketone 15 in Scheme 6, a variety of chain-elongated derivatives of segment A can be accessed. Also carrying out an ethylalumination ($Et_3Al$) in place of methylalumination ($AlMe_3$) will allow the introduction of an ethyl group (Et) at C16. In the same context, other groups such as alkyl and benzyl groups can also be introduced using the alternate stannylcupration-alkylation method by replacing iodomethane with other electrophiles in this reaction shown below in Example 6 and illustrated in Scheme 7. In addition the thiazole ring can be replaced by other cyclic, aromatic and heteroaromatic rings by using other vinyl or aromatic/heteroaromatic halides in place of 2-methyl-4-bromothiazole 17 in the coupling reaction following either the carboalumination or stannylcupration strategy exemplified in Schemes 6 and 7 respectively.

These aforementioned modifications are best illustrated by Formula E. Again all of these modified segments can then be utilized in the total synthesis of various analogs of epothilones.

EXAMPLE 6

Scheme 7 illustrates an alternative way to introduce the trisubstituted olefin. This method utilizes the stannylcupration-methylation methodology described by Harris, L., et al., in *Synthetic Approaches to Rapamycin 3. Synthesis of a C1–C21 Fragment,* Synlett, 903–905 (1996), the methodology of which is hereby incorporated by reference. Thus the O-TBS ether 16a from Scheme 7 of propargylic alcohol 16 on treatment with the stannylcuprate reagent 20 followed by methylation with iodomethane would provide the corresponding stannane which would then be coupled under Stille conditions with the bromothiazole 17 to yield the olefin 19.

EXAMPLE 7

The synthesis of 2-methyl-4-bromothiazole 17 from the known 2,4-dibromothiazole is outlined in Scheme 8. This 2,4-dibromothiazole has been previously reported by Reynaud, P., Robba, M. and Moreau, R. C. in *Sur une Nouvelle Synthese du Cycle Thiazolique,* Bull. Soc. Chim. Fr., 295:1735–1738 (1962), the teachings of which are hereby incorporated by reference.

EXAMPLE 8

This example illustrates the stereoselective construction of the C12–C13 cis-olefinic bond, the process of which is outlined in Scheme 9. The method shown provides maximum control over the olefin geometry as well as furnishes common intermediates in the synthesis of both epothilones A and B. This method is also amenable to introduction of affinity labels at C-12.

The C12–C13 olefin is constructed in the form of Z-vinyl iodides A that can be obtained from vinylstannanes with defined configurations. The vinyl stannanes will be accessed by using the chemistry reported by Lipshutz et al., in *Preparation of Z-Vinylstannanes via Hydrozirconation of Stannylacetylenes*, Tetrahedron Lett., 33:5861–5864 (1992) and Lipshutz, B. H. and Keil, R. in *Hydrozirconation/Transmetalation of Acetylenic Stannanes. New 1,1-Dimetallo Reagents*, Inorganica Chimica Acta, 220:41–44 (1994), the teachings of which are hereby incorporated by reference. The chemistry utilizes a 1,1-dimetallo species as a stereodefined 1,1-vinyl dianion synthon.

The synthesis starts with a Corey-Fuchs reaction (PPh$_3$, CBr$_4$), as described by Corey, E. J. and Fuchs, P. L., *A Synthetic Method for Formyl to Ethynyl Conversion*, Tetrahedron Lett., 36:3769–3772 (1972) of the known aldehyde 22, followed by base-induced elimination and quenching of the lithium acetylide with tributyltin chloride (Bu$_3$SnCl) to yield alkynylstannane 23. The 1,1-dimetallo species 24 is generated by hydrozirconation of the alkynyl stannane 23 using chlorohydridozirconocene (Schwartz reagent). An aqueous quench provides Z-vinylstannane 25a or alternatively, selective transmetalation with a higher order cuprate, followed by addition of an electrophile (MeOTf in case of epothilone B) to the resultant species provides the α-substituted vinylstannane 25b with high stereoselectivity. The Z-vinylstannanes 25a and 25b can then be transformed to the corresponding vinyl iodides A utilizing iodine with retention of configuration.

In summary, although the vinyl iodides A are previously reported compounds as evidenced by the teachings of Schinzer, D. et al., *in Total Synthesis of (–)-Epothilone A*, 36 Angew. Chem., Int. Ed. Engl., 523–524 (1997) and Schinzer, D., Bauer, A., and Scheiber, J., *Synthesis of Epothilones: Stereoselective Routes to Epothilone B*, Synlett, 861–864 (1998), the teachings of both are hereby incorporated by reference, the method to synthesize it from the known aldehyde 22 is different from conditions reported in other total syntheses of epothilones. In addition, the above mentioned hydrozirconation reactions provides precise control over the geometry of the C12–C13 olefin bond and this methodology constitutes a unique way to construct this double bond. Also the use of other electrophiles in the transmetalation reaction with the intermediate species 24 allows for the synthesis of various analogs modified at C12 position of the epothilones as illustrated in Formula E.

EXAMPLE 8A

This example illustrates the important steps in the chemistry depicted in Scheme 9B, for the production of vinyl halide C12–C20 precursors.
Synthesis of Enone 3

Barium hydroxide octahydrate (0.21 g, 0.68 mmol) was added to the beta-ketophosphonate 2 dissolved in 2.5 mL of anhydrous THF. After 45 minutes at room temperature, this mixture was cooled to 0° C. and the aldehyde 1 dissolved in 2.4 mL of THF and 0.12 mL of water was added dropwise. The reaction mixture was stirred at 0° C. for one hour and then warmed to room temperature over 45 minutes. The mixture was diluted with 10 mL of dichloromethane and 10 mL of saturated aqueous sodium bicarbonate was then added. The aqueous layer was extracted thrice with dichloromethane (5 mL) and combined organics dried over anhydrous magnesium sulfate. Flash column chromatography of the crude material after concentration on silica gel using a gradient of hexanes and diethyl ether (5% ether-hexanes to 30% ether-hexanes) gave 208 mg of the enone (75% yield).
Synthesis of Alcohol 4

(R)-Me-CBS-oxazaborolidine (0.08 mL, 0.08 mmol, 1M solution in toluene) was placed in a 10 mL flask and toluene was removed in vacuo. The residual solid was dissolved in 0.3 mL of dichloromethane and borane dimethylsulfide complex (0.23 mL, 0.23 mmol, 1M in dichloromethane) was added dropwise. This mixture was cooled to 0° C. and the enone 3 (0.05 g, 0.154 mmol) dissolved in 0.3 mL dichloromethane was added dropwise over a period of one hour. After stirring at 0° C. for two hours, methanol (0.5 mL) was carefully added followed by 1,2-ethanolamine (0.3 mL). The reaction mixture was stirred for another 16 hours at room temperature following which it was poured into 15 mL of ethyl acetate and washed with saturated aqueous ammonium chloride, water and brine. The organic layer was then dried over anhydrous magnesium sulfate, concentrated and the crude was then purified by flash column chromatography on silica gel using 70:30 hexanes:diethyl ether to 50:50 hexanes:diethyl ether solvent mixture as eluent. The desired alcohol was obtained in 70% yield (35 mg) and in 95% enantiomeric excess.
Synthesis of Bis-silylether 5

The alcohol 4 (0.24 g, 0.73 mmol) dissolved in 5 mL of dichloromethane was cooled to –78° C. and 2,6-lutidine (0.13 mL, 1.095 mmol) was added. TBSOTf(0.2 mL, 0.88 mmol) was then added. After stirring for 15 minutes, the reaction mixture was quenched with saturated aqueous ammonium chloride (5 mL) and then the aqueous layer was extracted thrice with dichloromethane. The combined organics were dried over anhydrous magnesium sulfate. Flash column chromatography of the crude after concentration using silica gel and 13:1 hexanes: diethyl ether as eluent provided 0.257 g (80% yield) of the known bis-silyl ether 5.

Example 8B

This example illustrates the chemistry depicted in Scheme 9C, using the known aldehyde 6 as a starting material to produce the desired vinyl halide precursor.
Synthesis of Alcohol 7

The enolate of ethyl acetate (1.76 mL, 18.0 mmol, 1.00 equiv) was generated at –78° C. using LDA (19.8 mmol, 1.10 equiv). The known aldehyde 6 was added dropwise and the reaction mixture turned bright orange. After 10 minutes the reaction was quenched with NH$_4$Cl (20 mL). Brine (20 mL) was added and the aqueous layer was extracted four times with Et$_2$O (50 mL). The combined organic layer was dried over MgSO$_4$ and concentrated. Column chromatography (hexane/ether gradient 1: 1, 3:1, 100% Et$_2$O) gave 3.5 grams (76% yield) of the desired alcohol 7.
Synthesis of Beta-ketoester 8

MnO$_2$ (23.4 grams, 10 wt %) was placed in dry chloroform (40 mL) and the temperature was lowered to 0° C. The alcohol 7 (2.34 grams, 1 equiv) was added to the MnO$_2$ suspension in chloroform (25 mL). The reaction was warmed to room temperature and stirred for 17 hours. The mixture was then filtered through Celite which was rinsed four times with CH$_2$Cl$_2$ (50 mL). The combined organic layer was dried (Na$_2$SO$_4$), concentrated, and passed through a short column with 100% Et$_2$O to provide 1.95 g (90%) of beta-ketoester 8.

Synthesis of Chiral Alcohol 9

Acetone and methanol were each degassed 5 times using the freeze-thaw method. (S)-BINAP (74 mg, 0.12 mmol, 15 mol%) and the ruthenium complex (38 mg, 0.12 mmol, 15 mol %) were combined in a two-neck flask with acetone (9 mL) and HBr solution (0.85 mL: 5.1 mL acetone and 0.25 mL 48% HBr). This mixture was stirred at room temperature for two hours, after which the acetone was removed under reduced pressure. The catalyst was transferred with MeOH (4 mL total) into a Parr flask containing the beta-ketoester 8 in MeOH (4 mL) total. (Beta-ketoester 8 in MeOH, 2 mL, was deoxygenated three times prior to transfer to Parr flask). The hydrogenation reaction was carried out for two hours at 52.5 psi and at room temperature. The MeOH was removed and the residue was redissolved in ether and filtered. Column chromatography in (1:1 hexane/Et$_2$O) provided 100 mg (50% yield) of the desired alcohol 9. The enantiomeric excess was determined to be 83% by chiral HPLC (95:5 hexane/EtOH, 254 nm, 1 mL/min, Chiracel OD—H).

Synthesis of Silyl Ether 10

The alcohol 9 (267 mg, 1.05 mmol, 1.00 equiv) was dissolved in CH$_2$Cl$_2$ (5 mL), and the temperature was lowered to 0° C. 2,6-lutidine (0.260 mL, 2.23 mmol, 2.13 equiv) was added followed by TBSOTf (0.375 L, 1.63 mmol, 1.55 equiv). The reaction was stirred for 1.5 hours and then quenched with water (2 mL). The mixture was extracted four times with CH$_2$Cl$_2$ and the combined organic layer was washed with brine, dried over Na$_2$SO$_4$, and concentrated. Column chromatography (3:1 hexane/Et$_2$O) gave 276 mg (72% yield) of the protected ester 10.

Synthesis of Primary Alcohol 11

The protected ester (275 mg, 1.03 mmol, 1.00 equiv)was dissolved in CH$_2$Cl$_2$ (5 mL) and the temperature was lowered to −78° C. DIBAL-H (5 mmol, 1.0 M in hexanes) was added dropwise and after 6 hours, the reaction was quenched with saturated potassium sodium tartrate (15 mL) and allowed to stir two hours until the phases had separated. The mixture was then extracted four times with CH$_2$Cl$_2$. The combined organic layers were dried over sodium sulfate (Na$_2$SO$_4$) and concentrated. After column chromatography (hexane/ether gradient 1:1, 3:1, 100% Et$_2$O), 80 mg of known alcohol 11 was obtained.

EXAMPLE 9

This example and the next (Example 10) illustrate C11–C12 bond construction including coupling of the C1–C11 (segment D) and C12–C20 (segment A) subunits and completion of the total synthesis.

Having defined all the requisite stereocenters and geometries, the stage is set for the union of the C1–C11 and the C12–C20 subunits. The C11–C12 bond connection is achieved by the B-alkyl Suzuki reaction of the C1–C11 olefin D with the vinyl iodides A shown in Scheme 10 to afford the precursors 26 for the synthesis of epothilone A and B. This B-alkyl Suzuki reaction is described by Miyaura, N., and Suzuki, A. in *Palladium-Catalyzed Cross-Coupling Reactions of Organoboron Compounds*, Chem. Rev. 95:2457–2483 (1995), the teachings of which are hereby incorporated by reference. Thus, hydroboration of the olefin D with 9-BBN followed by coupling of the corresponding organoborane with the vinyl iodides A in presence of [PdCl$_2$(dppf)$_2$] would yield the olefin 26.

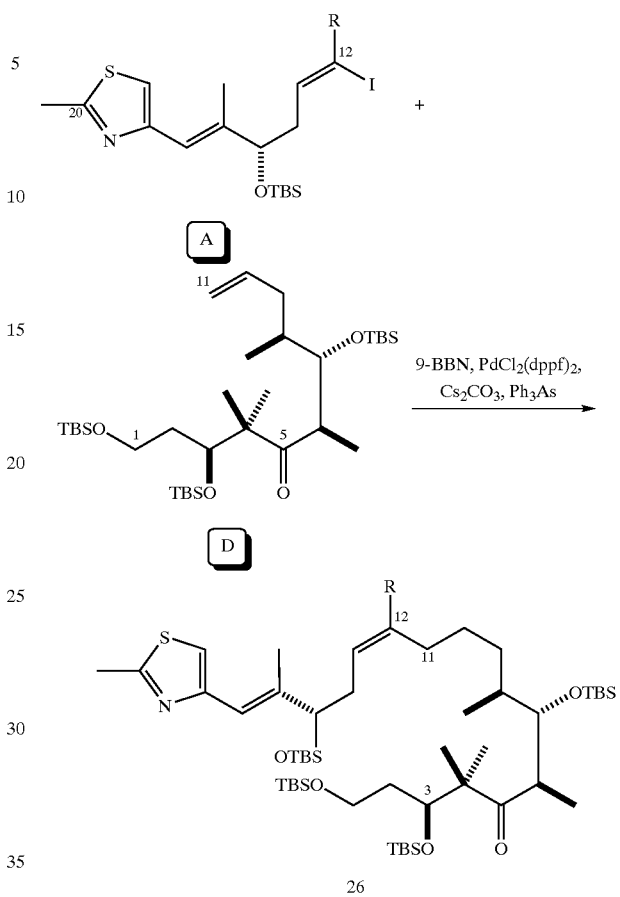

EXAMPLE 10

Finally the conversion of the coupled C1–C20 products 26 to epothilones A and B is accomplished using the previously reported procedures of Nicolaou, K. C. et al., in *Total Syntheses of Epothilones A and B via a Macrolactonization-Based Strategy* J. Am. Chem. Soc., 119:7974–7991 (1997), the teachings of which are hereby incorporated by reference. Thus selective deprotection at C1 by camphorsulfonic acid (CSA), shown in Scheme 11, followed by sequential oxidation of the primary alcohol first under Swern conditions followed by NaClO$_2$—NaH$_2$PO$_4$furnishes the known acids. Selective deprotection of the TBS ether at C15 using tetrabutylammonium fluoride yields the hydroxy acids 27. The key macrolactonization step is then carried out using the Yamaguchi method as descibed by Inanaga, J. et al., in *A Rapid Esterification by Means of Mixed Anhydride and its Application to Large-ring Macrolactonization*, Bull. Chem. Soc. Jpn., 52:1989–1993 (1979), the teachings of which are hereby incorporated by reference, affording the known 16-membered macrolides 28. The final stages in the synthesis involve the deprotection of both the TBS groups from the macrolides 28 (TFA, CH$_2$Cl$_2$) and the diastereoselective epoxidation of the C12–C13 double bond with epoxidizing agents such as dimethyldioxirane or methyl(trifluoromethyl)dioxirane.

Scheme 13

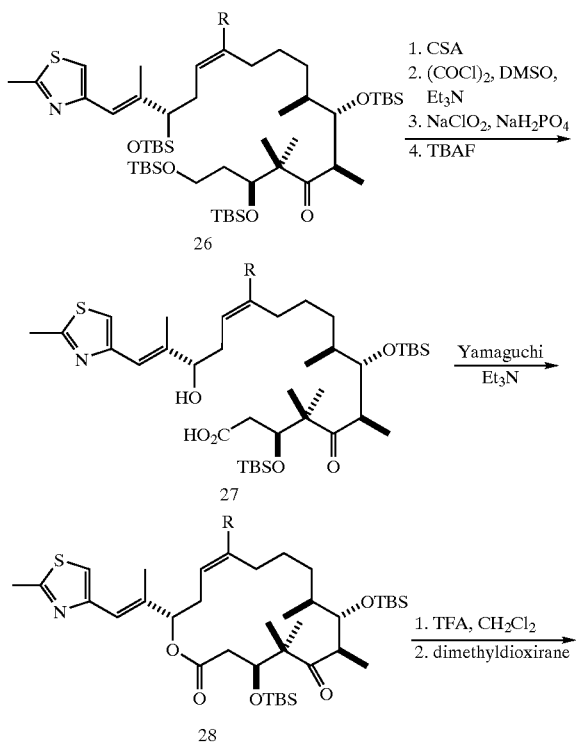

1a: R = H, epothilone A
1b: R = Me, epothilone B

As shown in Formulae I, IX and X, various modified segments can be employed during the syntheses of the individual segments (C, B and A). All of these modified segments can then be connected using the bond connections (Aldol reaction and the B-alkyl Suzuki reaction) highlighted in this total synthesis. This would provide numerous homologs, analogs and affinity labels of the epothilones. All references noted herein are expressly incorporated by reference.

Acronym and Symbol Definitions

In order to facilitate the preceding discussion various acronyms and symbols have been used. These have the following definitions.

| Ac | acetyl |
|---|---|
| Ar | aromatic |
| 9-BBN | 9-borabicyclo[3.3.1]nonane |
| (S)-BINAP | (S)-(-)-1,1'bi-2-naphthal(s)-(-)-2,2'-Bis(diphenylphosphino)1,1'binaphthyl |
| Bn | benzyl |
| BnO | benzyloxy |
| Bu | butyl |
| n-BuLi | n-butyl lithium |
| $Cp_2ZrCl_2$ | zirconocene dichloride |
| $Cp_2Zr(H)Cl$ | chlorohydridozirconocene |
| CSA | camphorsulfonic acid |
| DDQ | 2,3-dichloro-5,6-dicyano-1,4-benzoquinone |
| DIBAL-H | diisobutylaluminum hydride |
| DIEA | diisopropylethylamine |
| (+)DIPT | diisopropyl tartrate |
| DMF | N,N-dimethylformamide |
| DMPU | 1,3-dimethyl-3,4,5,6-tetrahydro-2(1H)pyrimidinone |
| DMSO | dimethylsulfoxide |
| ee | enantiomeric excess |
| Et | ethyl |
| HBTU | O-(benzotriazol-1-y-1)-N,N,N',N' tetramethyluronium hexafluoro phosphate |
| HF | hydrogen fluoride |
| HMPA | hexamethylphosphoramide |
| LDA | lithium diisopropylamide |
| LHMDS | lithium hexamethyldisilazide |
| LICA | lithium isopropylcyclohexylamide |
| m-CPBA | meta-chloroperoxybenzoic acid |
| MDR | multi-drug resistant |
| Me | methyl |
| MeOTf | methyl triflate |
| MS | molecular sieves |
| MsCl | mesyl chloride |
| NaHMDS | sodium hexamethyldisilazide |
| NMO | 4-methylmorpholine N-oxide |
| OTf | trifluoromethane sulfonate |
| $PdCl_2(dppf)_2$ | dichloro[1,1'-Bis(diphenylphosphino)ferrocene] palladium II |
| $Pd(PPh_3)_4$ | tetrakis (triphenylphosphine) palladium (0) |
| Ph | phenyl |
| $PPh_3$ | triphenylphosphine |
| PMB | para-methoxybenzyl |
| Ru cat | bis-(2 methylallyl) cycloocta-1,5-diene ruthenium (II) |
| TBAF | tetrabutylammonium fluoride |
| TBHP | tertbutyl hydroperoxide |
| TBS | tertiary-butyldimethylsilyl |
| TBSCl | tertiary-butyldimethylsilyl chloride |
| TBSOTf | tertiary-butyldimethylsilyl triflate |
| TFA | trifluoroacetic acid |
| THF | tetrahydrofuran |
| $Ti(O-iPr)_4$ | titanium isopropoxide |
| TPAP | tetrapropylammonium perruthenate |

We claim:
1. A method of synthesizing in high enantomeric excess an alcohol of the formula

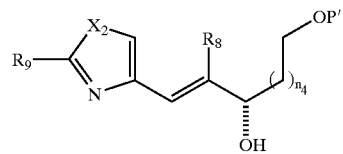

where $R_8$ is selected from the group consisting of H, C1–C4 straight or branched chain alkyl, alkenyl or alkynyl groups, $R_9$ is selected from the group consisting of H, C1–C10 straight and branched chain alkyl, alkenyl, alkynyl, hydroxyalkyl, hydroxyalkenyl and hydroxyalkynyl groups, substituted and unsubstituted cyclic, heterocyclic and aryl groups, $X_2$ is O or S, P' is a protective group, and $n_4$ is an integer which ranges from 1 to 4, said method comprising the step of:
providing an enone compound of the formula

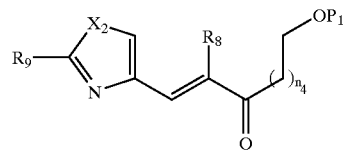

where $R_8$, $R_9$, $X_2$, P' and $n_4$ are as defined above; and asymmetrically reducing said enone compound in the presence of a chiral catalyst to obtain said alcohol.
2. The method of claim 1, including the step of providing said enone compound by reacting in a basic reactive medium an aldehyde compound of the formula

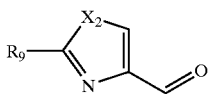

where $R_9$ and $X_2$ are as defined in claim 1, with a phosphonate compound of the formula

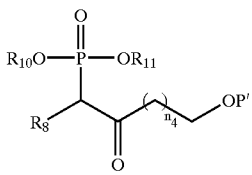

where $R_8$, P' and $n_4$ are as defined in claim 1, $R_{10}$ and $R_{11}$ are individually selected from the group consisting of C1–C4 straight or branched chain alkyl groups.

3. The method of claim 1, wherein $R_8$ and $R_9$ are each H, X is S, n is 1, and P' is TBS.

4. The method of claim 1, said asymmetric reduction reaction being carried out at a temperature of from about −20 to 40° C.

5. The method of claim 1, said chiral is preferably (R)-B-Me-CBS-oxazaborolidine.

6. A method of synthesizing the C12–C20 epothilone precursor of the formula

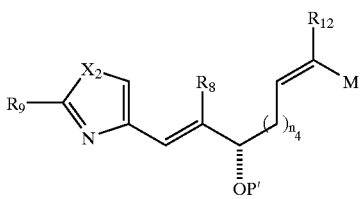

where $R_8$ is selected from the group consisting of H, C1–C4 straight or branched chain alkyl, alkenyl or alkynyl groups, $R_9$ is selected from the group consisting of H, C1–C10 straight and branched chain alkyl, alkenyl, alkynyl, hydroxyalkyl, hydroxyalkenyl or hydroxyalkynyl groups, substituted and unsubstituted cyclic, heteroxylic and aryl groups, $R_{12}$ is selected from the group consisting of H, C1–C10 straight and branched chain alkyl groups, substituted and unsubstituted benzyl groups, and C1–C10 alkoxy groups, $X_2$ is O or S, n is an integer which ranges from 1 to 4, P' is a protective group and M is either iodine or bromine, wherein an alcohol of the formula

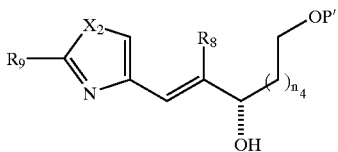

where $R_8$, $R_9$, $X_2$, $n_4$ are as defined above and P' is a protective group, is converted to the C12–C20 epothilone segment A, which method comprises the steps of:

providing an enone compound of the formula

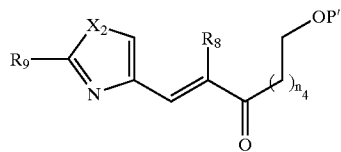

where $R_8$, $R_9$, $X_2$, P' and $n_4$ are as defined above; and asymmetrically reducing said enone compound in the presence of a chiral catalyst to obtain said alcohol.

7. The method of claim 6, including the step of providing said enone compound by reacting in a basic reactive medium an aldehyde compound of the formula

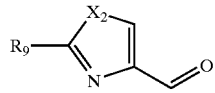

where $R_9$ and $X_2$ are as defined in claim 6, with a phosphonate compound of the formula

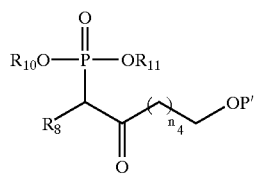

where $R_8$, P' and $n_4$ are as defined in claim 6, and $R_{10}$ and $R_{11}$ are individually and respectively selected from the group consisting of C1–C4 straight or branched chain alkyl groups.

8. The method of claim 6, wherein $R_8$ and $R_9$ are each H, X is S, $n_4$ is 1, and P' is TBS.

9. The method of claim 6, said chiral catalyst is preferably (R)-B-Me-CBS-oxazaborolidine.

10. A method of synthesizing the C12–C20 epothilone precursor of the formula

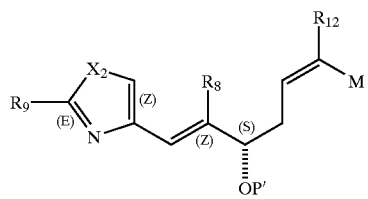

where $R_8$ is selected from the group consisting of H, C1–C4 straight or branched chain alkyl, alkenyl or alkynl groups, $R_9$ is selected from the group consisting of H, C1–C10 straight and branched chain alkyl, alkenyl, alkynl, hydroxyalkyl, hydroxyalkenyl and hydroxyalkynl groups, substituted and unsubstituted cyclic, heteroxylic and aryl groups, $R_{12}$ is selected from the group consisting of H, C1–C10 straight and branched chain alkyl groups, substituted and unsubstituted benzyl groups, and C1–C10 alkoxy groups, $X_2$ is O or S, n is an integer which ranges from 1 to 4, P' is a protective group and M is either bromine or iodine, said method comprising the steps of:

providing an aldehyde of the formula

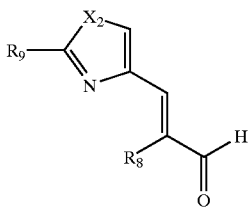

where $R_8$, $R_9$, and $X_2$ are as defined above;
reacting said aldehyde with an acetate of the formula

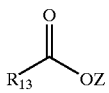

where $R_{13}$ is a C1–C4 alkyl group, Z is a C1–C4 straight or branched chain alkyl group or a substituted or unsubstituted benzyl group in a basic reaction mixture to yield a β-hydroxyester of the formula

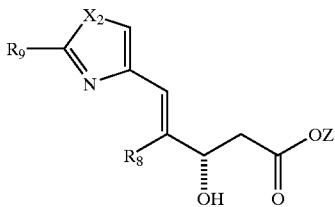

where $R_8$, $R_9$, $X_2$, Z and $n_4$ are as defined above;
oxidizing said β-hydroxyester to the corresponding β-ketoester of the formula

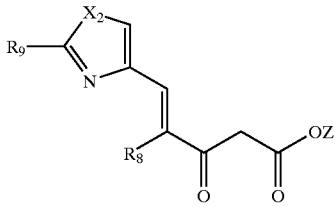

where $R_8$, $R_9$, $X_2$, Z and $n_4$ are as defined above;
hydrogenating said β-ketoester to form a chiral alcohol of the formula

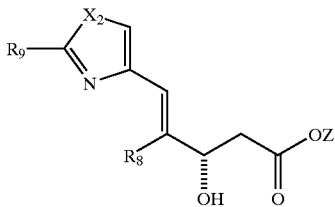

where $R_8$, $R_9$, $X_2$, Z and $n_4$ are as defined above, by reacting the β-ketoester with a hydrogenating agent in the presence of asymmetric organometallic molecular catalyst comprising a metal atom or ion having one or more chiral ligands coupled thereto; and
converting said chiral alcohol to said C12–C20 epothilone precursor.

11. The method of claim 10, said acetate being ethyl acetate.

12. The method of claim 10, wherein said aldehyde and acetate are reacted in the presence of an alkali metal diisopropyl amide in a solvent selected from the group consisting of THF, a mixture of t-butanol and t-butoxide, sodium ethoxide, and ethanol.

13. The method of claim 10, wherein said aldehyde and acetate are reacted at a temperature of from about −50 to −125° C.

14. The method of claim 10, wherein said β-hydroxyester is oxidized using an alkali metal or alkaline earth metal oxide or hydroxide.

15. The method of claim 10, wherein said hydrogenating agent is hydrogen.

16. The method of claim 10, said hydrogenating step being carried out at a pressure of from about 30–100 psi.

17. The method of claim 10, said hydrogenating step being carried out at a temperature of from about 40–100° C.

18. A method of synthesizing a C1–C6 epothilone precursor of the formula

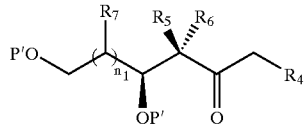

where $n_1$ is an integer from 0–4, $R_4$ is selected from the group consisting of H, C1–C10 straight and branched chain alkyl groups, substituted and unsubstituted benzyl groups, and C1–C10 alkoxy groups, $R_5$ and $R_6$ are each individually and respectively selected from the group consisting of H, substituted and unsubstituted aryl and heterocyclic groups, C1–C10 straight and branched chain alkyl groups, and substituted and unsubstituted benzyl groups, $R_7$ is H or straight or branched chain C1–C10 alkyl groups, and P' is a protective group, comprising the steps of:
providing a nitrile compound of the formula

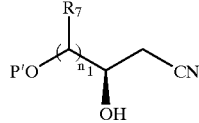

where P', $R_5$, $R_6$, $R_7$ and $n_1$ are as defined above, and the value of each $n_1$, may be the same or different;
alkylating said nitrile compound to yield a dialkylated compound of the formula

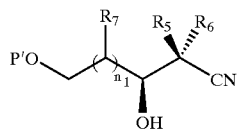

where P', $R_5$, $R_6$, $R_7$, and $n_1$ are as defined above, and the value of each $n_1$ may be the same or different; and
converting said nitrile compound to yield said epothilone precursor.

19. The method of claim 18, said converting step comprising the steps of oxidizing said dialkyated compound to yield a ketone of the formula

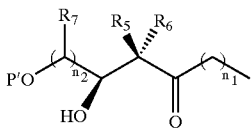

where P', $R_4$, $R_5$, $R_6$, and $n_1$ are as defined in claim 18; and converting said ketone to said C1–C6 epothilone precursor.

20. The method of claim 18, said converting step comprising the steps of deprotecting said nitrile compound to yield a diol compound having the formula

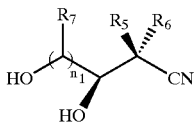

where $R_4$, $R_5$, $R_6$, $n_1$ are as defined in claim 18, and thereafter converting said diol compound to said C1–C6 epothilone precursor.

21. A method of synthesizing a C1–C6 epothilone precursor of the formula

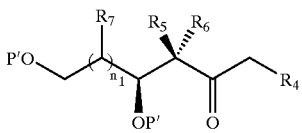

where $n_1$ is an integer from 0–4, $R_4$ is selected from the group consisting of H, C1–C10 straight and branched chain alkyl groups, substituted and unsubstituted benzyl groups, and C1–C10 alkoxy groups, $R_5$ and $R_6$ are each individually and respectively selected from the group consisting of H, substituted and unsubstituted aryl and heterocyclic groups, C1–C10 straight and branched chain alkyl groups, and substituted and unsubstituted benzyl groups, $R_7$ is H or straight or branched chain C1–C10 alkyl groups, and P' is a protective group, said method comprising the steps of: providing an ester compound of the formula

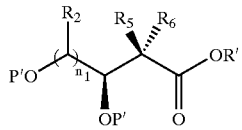

where $R_1$, $R_5$, $R_6$, $R_7$, $n_1$ and P' are as defined above, and R' is a C1–C10 striaght or branched chain alkyl group;

reacting said ester compound with a sulfone to acylate the ester, and thereafter desulfonating the acylated ester to obtain said epothilone precursor.

22. The method of claim 21, said sulfone being of the formula

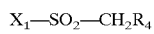

$$X_1-SO_2-CH_2R_4$$

where $X_1$ is selected from the group consisting of C1–C10 straight and branched chain alkyl, alkenyl, and alkynyl groups, and substituted and unsubstituted aryl and heterocyclic groups, and $R_4$ is as defined above.

23. The method of claim 22, said sulfone being ethyl phenyl sulfone.

* * * * *